US010132781B2

(12) United States Patent
Steingart et al.

(10) Patent No.: US 10,132,781 B2
(45) Date of Patent: Nov. 20, 2018

(54) APPARATUS AND METHOD FOR DETERMINING STATE OF CHANGE (SOC) AND STATE OF HEALTH (SOH) OF ELECTRICAL CELLS

(71) Applicant: The Trustees of Princeton University, Princeton, NJ (US)

(72) Inventors: Daniel Artemus Steingart, Princeton, NJ (US); Shoham Bhadra, North Brunswick, NJ (US); Andrew Hsieh, Princeton, NJ (US); Benjamin Hertzberg, Princeton, NJ (US); Peter James Gjeltema, Stow, MA (US); Clarence Worth Rowley, III, Princeton, NJ (US); Alexandre S. R. Goy, Lawrenceville, NJ (US); Jason Wolf Fleischer, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 530 days.

(21) Appl. No.: 14/610,219

(22) Filed: Jan. 30, 2015

(65) Prior Publication Data
US 2016/0223498 A1    Aug. 4, 2016

(51) Int. Cl.
*G01N 29/44*  (2006.01)
*G01N 29/04*  (2006.01)
(Continued)

(52) U.S. Cl.
CPC ....... *G01N 29/4427* (2013.01); *G01N 29/043* (2013.01); *G01N 29/07* (2013.01);
(Continued)

(58) Field of Classification Search
CPC .......... G01N 29/4427; G01N 29/4436; G01N 29/043; G01N 29/07; G01N 29/46; G01N 2291/0231; G01N 2291/2698
(Continued)

(56) References Cited

U.S. PATENT DOCUMENTS 4,442,700 A * 4/1984 Swoboda ............... G01N 9/24
                                                    73/32 A
6,520,018 B1 * 2/2003 Flores-Lira ........... G01N 29/11
                                                    73/629

(Continued)

OTHER PUBLICATIONS

J. Backman, et al., "Rechargeable Battery Condition Monitoring using Vibrational Properties", Product Compliance Engineering (ISPCE), 2014 IEEE Symposium, May 5-7, 2014, ISBN: 978-1-4799-5682-1, pp. 50-53, San Jose, CA.

*Primary Examiner* — Manish S Shah
*Assistant Examiner* — Rose M Miller
(74) *Attorney, Agent, or Firm* — Muncy, Geissler, Olds & Lowe, P.C.; Shankar Krithivasan

(57) ABSTRACT

A method, an apparatus and a system for interrogating a battery in order to determine one or more of: (i) its state of charge (SOC), (ii) its state of health (SOH), (iii) physical state of one or more internal components or parts, which utilizes at least one sound source for transmitting a signal (e.g., a sound wave or sound pulse through or across the battery, and at least one sound receiver for receiving a signal from the battery, which received signal is representative of the physical state of the battery being interrogated. The interrogation method is noninvasive, namely does not require the depletion of a portion of the charge of the battery being tested or settlement or the destruction of the battery in order to evaluate one or more of (i), (ii) and (iii).

30 Claims, 15 Drawing Sheets

(51) Int. Cl.
    *G01N 29/07*     (2006.01)
    *G01N 29/46*     (2006.01)

(52) U.S. Cl.
    CPC ......... *G01N 29/4436* (2013.01); *G01N 29/46* (2013.01); *G01N 2291/0231* (2013.01); *G01N 2291/2698* (2013.01)

(58) Field of Classification Search
    USPC .................. 73/602, 579, 582, 597, 598, 627
    See application file for complete search history.

(56) References Cited

U.S. PATENT DOCUMENTS

| | | | | |
|---|---|---|---|---|
| 2008/0133156 | A1* | 6/2008 | Redko | H01M 10/4285 |
| | | | | 702/63 |
| 2012/0148880 | A1* | 6/2012 | Schaefer | H01M 10/48 |
| | | | | 429/50 |
| 2013/0269436 | A1* | 10/2013 | Couse | G01N 29/12 |
| | | | | 73/582 |
| 2013/0335094 | A1* | 12/2013 | Adams | G01R 31/3606 |
| | | | | 324/426 |
| 2016/0084911 | A1* | 3/2016 | Mensah-Brown | |
| | | | | G01R 31/3606 |
| | | | | 318/139 |
| 2016/0141732 | A1* | 5/2016 | Kuhne | G01F 23/296 |
| | | | | 429/50 |
| 2016/0197382 | A1* | 7/2016 | Sood | G01R 31/3679 |
| | | | | 429/92 |

* cited by examiner

APPARATUS AND METHOD FOR DETERMINING STATE OF CHANGE (SOC) AND STATE OF HEALTH (SOH) OF ELECTRICAL CELLS

STATEMENT REGARDING FEDERALLY SPONSORED RESEARCH OR DEVELOPMENT

This invention was made with U.S. Federal government support under Grant No. CMMI-1402872 awarded by the National Science Foundation and under Grant No. DE-AR0000400 awarded by the Department of Energy, Advanced Research Projects Agency. The U.S. Federal government has certain rights in the invention.

BACKGROUND OF THE INVENTION

Presently known are ultrasonic testing methods for solid materials, such as metals, weld joints, or composite materials which may be evaluated by ultrasonic testing methods in order to determine their relative density; such testing methods are substantially limited to establishing the physical strength of such materials. Such solid materials however are ones which have a density and/or other physical characteristics which do not appreciably change during their service life.

Electrical devices, including electronic devices, are ubiquitous. Such devices rely upon power sources for their operation and increasingly, such electrical devices rely on one or more electrochemical cells, hereinafter referred to as a "battery". Batteries are found in portable devices (i.e., electronic devices including telecommunications devices including cell phones, computers, tablets), vehicles (i.e., aircraft, automobiles, boats, etc.) as well as in non-portable applications (i.e., power supplies, backup batteries for mains powered electrical devices). The proliferation of such devices is expected to increase in the indefinite future, and with it the use of batteries to power such devices. Such batteries may be of any variety of chemistries and/or configurations, the only requirement being that they can be used as a power source for electrical and/or electronic devices. Presently, common battery types include so-called "wet cell" lead-acid batteries containing a liquid electrolyte which are still often found in high amperage applications, such as in automobiles, backup batteries and power supplies, as well as in alarm systems. Of growing prevalence are so-called "dry cell" battery types which include a non-liquid electrolyte, with the most common types being rechargeable nickel cadmium (NiCd) and nickel metal hydride (NiMH) type batteries, rechargeable lithium-ion (Li-ion) batteries including Graphite/LiNMC and Graphite/LiNCA type batteries, and non-rechargeable $Zn$—$MnO_2$ (alkaline) type batteries. The latter non-liquid electrolyte type batteries find prominent utility in vehicles as well as in portable electrical and/or electronic devices, and are available in a plethora of configurations. Most are either characterized as single-use type batteries intended to be disposed after discharge, or rechargeable type batteries which can be recharged, and are used a number of times.

With the increasing use of such batteries, and their widespread presence in devices, vehicles, etc., there is a growing need for methods of monitoring the performance characteristics of these batteries. Two such performance characteristics include a "state of charge" (SOC) of the battery, which is related to the amount of current which may yet be supplied by the battery in its particular state, and "state of health" (SOH) of the battery, which is related to the overall physical state of the battery and/or its performance characteristics. Such performance characteristics may include predicted performance characteristics, as well as actual performance characteristics.

Present methods for determining the SOC and/or SOH of a battery usually require an invasive technique which may either degrade or destroy the battery, or require that the battery be discharged when seeking to determine the SOC and/or SOH. Such techniques are frequently impractical; the best case scenario requires depletion of some of the battery charge while providing little information concerning the internal construction features of the battery, and in the worst case scenario the battery under evaluation is incapacitated or destroyed and cannot be reused. One recently proposed technique and apparatus is the mechanical measurement technique and apparatus disclosed in US 2014/0107949 describing the use of a load cell and a stress/strain sensor mechanically coupled to a battery, and used to determine mechanical battery and/or cell expansion. The apparatus is useful in measuring the stress as well as the strain which is stated to be relevant to the SOC and the SOH of the battery. However, the technique provides little information regarding the physical state of the internal components or parts of the battery, e.g., anode, cathode, separator layer(s), merely from the stress and/or strain readings provided. The technique also requires the removal of the battery from the device in which it is installed, and subsequent placement within the disclosed apparatus for measuring stress and strain.

Accordingly, there exists a real and urgent need in the art for an improved method, apparatus and system for determining the SOC and/or SOC of a battery. There also exists a real and urgent need in the art for a noninvasive technique for evaluating the physical state of one or more internal components or parts of a battery.

SUMMARY OF THE INVENTION

Broadly, the present invention provides a noninvasive method, an apparatus and a system for interrogating a battery to evaluate its condition at the time of its interrogation. The evaluated condition may be used to determine one or more of: (i) its state of charge (SOC), (ii) its state of health (SOH), (iii) physical state of one or more internal components or parts. The method utilizes at least one sound source means for transmitting a signal (e.g., a sound wave or sound pulse) through a part of or across the battery, and at least one sound receiver means for receiving a signal from the battery; the received signal includes information representative of the physical state of the battery being interrogated. The interrogation method is noninvasive; namely, it does not require any electrical contact with the battery which would lead to the depletion of a portion of the charge of the battery being tested, nor does it require the disassembly of or the destruction of the battery, in order to evaluate one or more of (i), (ii) and (iii).

In a broad aspect the method, apparatus and system provides a non-invasive method of probing a battery for changes in density and/or elastic modulus of one or more component parts of the battery, preferably in the anode and cathode thereof, and/or to probe the battery for changes in density or modulus distribution of one or more component parts of the battery, in a noninvasive (or nondestructive) which can be operated in real time, whereby the battery is interrogated using sound waves transmitted into and/or through the battery. The method, apparatus and system utilizes a sound source means for generating a suitable sound signal, and a sound receiver means for collecting responsive signal(s) received from the battery, operatively coupled to a processor means which may be used to derive data and information from the collected signal(s) relevant to one or more of the battery's: (i) state of charge (SOC), (ii) state of health (SOH), (iii) physical state of one or more internal components or parts of the interrogated battery. Such a determination may be by the processor means comparing data and information derived from the received signals with a data set present in a data storage means operatively coupled to the processor means. The processor means may also process data and information received by the sound receiver means and store the processed data and information as a data set or a reference data set in the data storage means, which may be used in a subsequent noninvasive interrogation of a battery.

More specifically, in one aspect there is provided an apparatus which includes a sound source means, and a sound receiver means, preferably one or both of which may be one or more transducers. The apparatus further includes at least one controller means operatively coupled to the sound source means, whereby the controller means can be used to control the frequency and amplitude of the sound source such that a controlled signal, such as one or more sound waves, but preferably one or more ultrasonic pulses having a specific amplitude (alternately a specific driving force) and frequency, is transmitted from the sound source and into the battery under interrogation such that the controlled signal is transmitted through one or more of the internal components or parts of a battery. The sound receiver means which collects a signal received from the battery in response to the transmitted control signal may be operatively coupled to either a signal receiver means or the controller means, each of which is in turn operatively coupled to the processor means. The collected signal may be a transmitted signal which has passed through one or more parts of the battery, a reflected signal which has been reflected from one or more parts of the battery or may include both. A processor means is also present which includes a data processor and a data storage means. The data storage means may be used to contain information and data derived from the collected signal, which may be used by the data processor to determine one or more of the: (i) state of charge (SOC), (ii) state of health (SOH), (iii) physical state of one or more internal components or parts of the battery being interrogated. The data processor means may be used to generate and store a data set derived from the collected signals of the battery being tested, enabling a data set to be stored in the digital storage means. The data processor means may be used to generate data and information derived from the collected signals of the battery being tested, however without storing the derived data and information in the data storage means, but may instead compare said derived data and information with a data set previously stored in the digital storage means. The data processor means may perform one or more calculations, such as frequency filtering, or integration of data received by the processor means. The data set may be used by the data processor means for a later comparison with further data generated from the interrogation of a further battery of similar type. The data set includes information relevant to one or more of (i), (ii) and (iii) and/or other physical parameters of a tested battery, which information may be present as a look-up table of data values containing data relevant to the tested battery. Alternately the information indicative of one or more of (i), (ii) or (iii) of the tested battery may be represented by a linear or non-linear mathematical equation or approximation. Alternately the information indicative of one or more of (i), (ii) or (iii) of the tested battery may be stored as one or more data points representative of (i), (ii) or (iii), or may be an averaged value or other calculated value based derived from of one or more data points representative of (i), (ii) or (iii) particularly wherein the averaged value is of a plurality of data points during an interval of time. The time interval may be in fractions of a second, seconds, minutes or hours. The apparatus is operated to interrogate a battery ("test battery") in real time by transmitting one or more sound waves, collecting one or more signals from the test battery which are responsive to said one or more sound waves, providing representative data derived from the interrogation to the processor means which is operated to store data representative of the one or more received signals in the data storage means as a data set, and/or the processor means is used to compare data and information derived from one or more of the received signals from the test battery being interrogated with a data set stored in the data storage means to provide information indicative of the condition of the test battery at the time of its interrogation. The comparison of the data and information derived from the test battery may be compared by the processor means relative to a data set stored in the data storage means, with comparison by the processor means providing an indication of one or more of (i) its state of charge (SOC), (ii) its state of health (SOH), (iii) physical state of one or more internal components or parts of the test battery. The information relevant to one or more of (i), (ii), and (iii) may be optionally used to set an alarm condition concerning one or more of the (i), (ii) and/or (iii) wherein a fault or failure condition of a test battery has occurred, or is expected to occur. Such a fault condition may be, for example, wherein the interrogated battery fails to meet present or expected future performance characteristics.

In a further aspect of the invention, there is provided an apparatus which includes a sound source means, and a sound receiver means, preferably one or both of which may be one or more transducers. The apparatus further includes at least one controller means operatively coupled to the sound source means which controller means can be used to control the frequency and amplitude of the sound source such that a controlled signal, such as one or more sound waves, but preferably one or more ultrasonic pulses having a specific amplitude and frequency, is transmitted from the sound source and into the battery under interrogation such that the controlled signal is transmitted through one or more of the internal components or parts of a reference battery. A reference battery is a battery of a particular type which is deemed or determined to exhibit satisfactory technical performance characteristics representative of the particular type of battery that may be used as a reference standard for the particular type of battery against which the performance characteristics of other batteries of the same type may be evaluated. The sound receiver means which collects a signal received from the reference in response to the transmitted control signal may be operatively coupled to either a signal receiver means or the controller means, each of which is operatively coupled to the processor means. The collected signal may be a transmitted signal which has passed through one or more parts of the reference battery, a reflected signal which has been reflected from one or more parts of the reference battery, or may include both. A processor means is also present which includes a data processor and a data storage means. The data storage means may be used to contain information and data derived from the collected signal, which may be used by the data processor to determine one or more of the: (i) state of charge (SOC), (ii) state of health (SOH), (iii) physical state of one or more internal components or parts of the reference battery being interrogated. The processor means may be used to generate and store a data set derived from the collected signals of the reference battery being tested, which data set is stored in the digital storage means, and is representative of a "reference data set". The processor means may perform one or more calculations, such as frequency filtering, or integration of data received by the processor means. The reference data set may be used by the processor means for a later comparison with further data and information generated from the interrogation of a further battery of similar type. The reference data set includes information relevant to one or more of (i), (ii) and (iii) and/or other physical parameters of a tested battery, which information may be present as a look-up table of data values containing data relevant to the tested battery. Alternately the information indicative of one or more of (i), (ii) or (iii) of the tested battery may be represented by a linear or non-linear mathematical equation or approximation. Alternately the information indicative of one or more of (i), (ii) or (iii) of the tested battery may be stored as one or more data points representative of (i), (ii) or (iii), or may be an averaged value or other calculated value based derived from of one or more data points representative of (i), (ii) or (iii) particularly wherein the averaged value is of a plurality of data points during an interval of time. The time interval may be in fractions of a second, seconds, minutes or hours. The apparatus is operated to interrogate a reference battery in real time by transmitting one or more sound waves, collecting one or more signals from the test battery which are responsive to said one or more sound waves, providing representative data derived from the interrogation to the processor means which is operated to store data representative of the one or more received signals in the data storage means as a reference data set for the particular battery type.

Such a reference data set also provides a "fingerprint" of the: (i) state of charge (SOC), (ii) state of health (SOH), (iii) physical state of one or more internal components or parts of the reference battery, which the inventors have found differ between different battery types and/or chemistries. Such a finding provides a method for identifying a battery of unknown type using a noninvasive method disclosed herein, wherein derived data and information from responsive signals received from the battery of unknown type is used in a comparison by the processor means with one or more reference data sets stored in the data storage means which comprises one or more data sets of batteries of differing types and/or chemistries, and as a result of the comparison identifying the type and/or chemistry of the interrogated battery with the most similar reference data set of a reference battery of known chemistry and/or type.

In a further aspect the present invention provides a method for noninvasively determining one or more of the: (i) state of charge (SOC), (ii) state of health (SOH), (iii) physical state of one or more internal components or parts of a battery ("tested battery") by interrogating the battery utilizing at least one sound source means, and at least one sound receiver means, by contacting a part of a battery to be interrogated, or alternately placing at least one sound source means, and at least one sound receiver means in sufficient proximity with a part or surface of a battery being interrogated such that a controlled sound signal, e.g, at least one sound wave, but preferably at least one sound pulse having a specific amplitude and frequency is transmitted into the battery such that the sound wave, preferably at least one sound pulse, is transmitted through one or more of the internal components or parts of the battery. Thereafter at least one sound receiver means is used to collect a received signal responsive to the at least one sound wave, preferably at least one sound pulse, which received signal or information is processed by a processor means to derive data or information relevant to one or more of the tested battery's: (i) state of charge (SOC), (ii) state of health (SOH), and/or (iii) physical state of one or more internal components or parts of the tested battery. The processor means may be operated to store the received signal or information, and/or store derived data or information relevant to one or more of the tested battery's: (i) state of charge (SOC), (ii) state of health (SOH), and/or (iii) physical state of one or more internal components or parts of the test battery in a data storage means as a data set. The data storage means may be used to store information indicative of one or more of the (i) state of charge (SOC), (ii) state of health (SOH), (iii) physical state of one or more internal components or parts of the tested battery, which may be used a baseline for a particular battery type. The processor means may perform one or more calculations, such as frequency filtering, or integration of data received by the processor means. Data and information indicative of one or more of (i), (ii) and (iii) of a reference battery, and/or other physical parameters viz. a "reference data set", may already be present as a look-up table of data values containing data relevant to a tested battery, or such data may be the actual data and/or may be a linear or nonlinear approximation of actual data. Alternately, data and information relevant to one or more of (i), (ii) and (iii) of the test battery and/or other physical parameters of the test battery may be provided by the data means to the data storage means to form a "data set", which may be a look-up table of data values containing data relevant to the test battery, or such data may be the actual data and/or may be a linear or nonlinear approximation of actual data. Alternately the information indicative of one or more of (i), (ii) or (iii) of either the reference data set and/or the data set may be stored as one or more data points representative of (i), (ii) or (iii), or may be an averaged value or other calculated value based derived from of one or more data points representative of (i), (ii) or (iii) particularly wherein the averaged value is of a plurality of data points during an interval of time. The time interval may be in fractions of a second, seconds, minutes or hours. The processor means may be used to evaluate or compare a data set or reference data set present in the data storage means with further datum or data sets obtained according to the method from different further tested batteries, preferably of the same or similar types. The processor means may be used and operated to derive or calculate a relationship between data sets derived from two or more different batteries, e.g, two different "tested batteries", one or more "tested batteries" and one or more "reference batteries", etc. The relationship may be used to evaluate or predict one or more of (i) state of charge (SOC), (ii) state of health (SOH), and/or (iii) physical state of one or more internal components or parts of the interrogated test battery. The relationship may be optionally used to set an alarm condition concerning one or more of the (i), (ii) and/or (iii) wherein a fault or failure condition of a battery has occurred, or is expected to occur.

In a still further aspect the present invention provides a system for noninvasively determining one or more of the: (i) state of charge (SOC), (ii) state of health (SOH), (iii) physical state of one or more internal components or parts of a battery, which system includes an apparatus is described above and/or further described in this patent specification, which is operated in order to determine one or more of (i), (ii) and/or (iii) by operating the apparatus in accordance with a method described above and/or further described in this patent specification.

These and further aspects of the invention are described with more particularity hereinafter.

DETAILED DESCRIPTION

Figure 1:
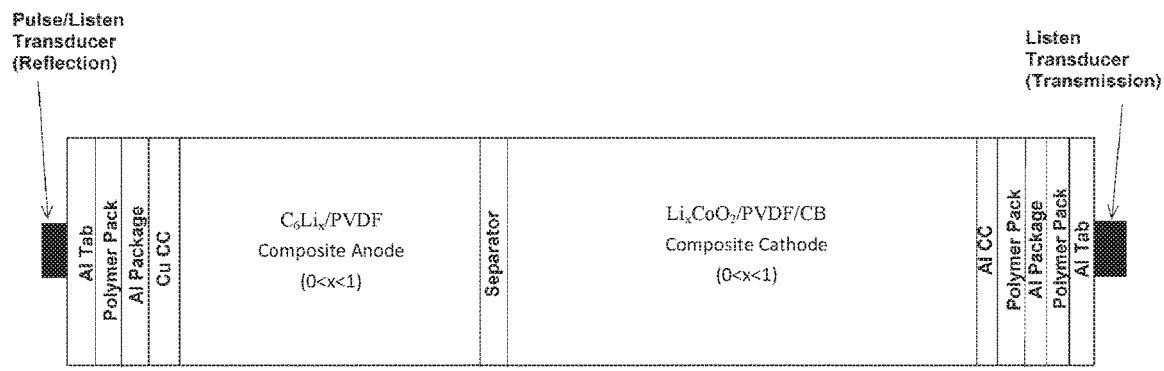
FIG. 1 illustrates a schematic view of a conventional Li ion battery.

As used herein, the term "battery" or "batteries" include a single electrical cell as well as a device which includes one or more electrical cells either connected in series or in parallel which are provided in a device or package. Regardless of their specific type, batteries comprise a plurality of internal components, each component made of a material which has specific material properties, e.g, a specific density and elastic modulus. An example of a typical battery comprising a single electrical cell is depicted on FIG. 1, which represents a cross-section of an "AA" type lithium ion battery as is commonly used in many electrical devices. As is seen therefrom the battery includes (beginning from the left end or terminal of the battery), a metal tab (here aluminum) as a terminal, a polymer layer, metal packaging (aluminum), a further polymer layer, a metal current collector (copper), a composite anode ($C_6Li_x$/PVDF), a separator layer, a composite cathode layer ($Li_xCoO_2$/PVDF/CB), a further metal current collector (here aluminum), a polymer layer, further metal packaging (aluminum), a polymer layer and finally a further metal tab (aluminum) as the right end or other terminal of the battery.) Batteries may include those which are constructed to hold a single charge and after the charge is substantially depleted, thereafter disposed. Of increasing importance and use however are batteries which may be recharged for reuse following their substantial depletion. While costlier than the former type of single use batteries, rechargeable batteries are frequently used in many types of portable electronics devices, e.g, computers, computer tablets, cellphones, etc.

The present inventors have discovered that the charge level of a battery at any point in time is a controlling factor in the physical state of the of the anode and cathode at that point in time, and that a variation in the charge level of the said battery introduces a corresponding change in the physical state of the of the anode and cathode, specifically in the density and the elastic modulus thereof. By the use of the apparatus and a system according to the invention and described herein, data collected at one or more charge levels of the battery can be analyzed to provide a reliable indication of one or more of the (i) its state of charge (SOC), (ii) its state of health (SOH), (iii) physical state of one or more internal components or parts of a battery being interrogated according to the noninvasive method described herein. The charge level of a battery strongly influences the physical properties of the anode and cathode which properties change with changing charge levels of the battery. The charge level of a battery may also affect other materials within the battery other than the anode and cathode. Noninvasive interrogation of a battery at different charge levels using sound waves, preferably ultrasonic sound waves or pulses, preferably over one or more, especially preferably over a large plurality (preferably 10, more preferably 100 or more) charge and discharge cycles of a battery being interrogated permits the collection of one or more responsive sound signal(s) transmitted into the battery from the one or more one sound source means, preferably across the battery and through the internal components or parts thereof. Collection and analysis of responsive sound signal(s) received from the battery provides information and characteristic data indicative of the operational status of the battery at its physical state, e.g., its present charge level at the time of the interrogation. The collected responsive sound signal(s) is quantitatively analyzed using known art analytical methods, e.g, wavelet analysis of vectors, fourier transformation, which are performed using a processor means. From this information, one or more of (i), (ii) and (iii) can be determined and/or predicted. A data set collected from such a noninvasive interrogation may be used in a subsequent comparison against a different data set or data sets representative of the performance characteristics of similar or dissimilar batteries which are undergoing or which had undergone a like noninvasive method of interrogation. Such a subsequent comparison is also quantitatively analyzed using known art analytical methods, e.g, comparing a wavelet analysis of vectors between data sets, comparing the fourier transforms between the data sets, by performing a Bayesian analysis of the data sets, which comparison is performed by a processor means, and the comparison statistically analyzed for a degree of deviation. One or more data sets obtained by this method may be used as a "reference data set" representative of a "reference battery", which may be used as a reference or baseline data set for comparison against the data sets of one or more similar batteries to be interrogated, undergoing interrogation or already having been interrogated by the noninvasive method, which may be useful in comparing and/or predicting the future performance characteristics of said one or more similar batteries. The data set obtained from the noninvasive interrogation method may also be used to provide physical state of one or more internal components or parts of a battery being interrogated, viz., the "test battery" or "tested battery". Such is particularly relevant to determining the current existence of, or the potential likelihood of a change in the physical structure of one or more of the internal components which may result in the failure of the battery.

In establishing a "reference data set" or a "data set", subsequent to collection of one or more response signals and subsequent quantitative analysis of the collected response signals, if desired the interrogated battery may be disassembled and its component parts inspected and analyzed in order to determine the physical state of the battery, which provides information and data relevant to the State of Charge (SOC) and/or the State of Health (SOH) of the battery, which information and data may be correlated to one or more of the response signals received from the battery prior to its disassembly. The inventors have found that during one or more charge/discharge cycles of a battery, further physical changes other than to the specific density and elastic modulus may occur, i.e., a change in the physical state of one or more of the internal components or parts of the battery including but not limited to: structural relaxation related transport phenomena due to establishment of open circuit potential, a phase change, a mechanical strain, the formation of a fracture in the material of an internal component, swelling, dissolution, of one or more of the internal components of the battery, or the deposition of materials upon one or more of the surfaces of one or more of the internal components of the battery (viz., passivation). Such are non-limiting examples of physical changes in a battery which may be evaluated by the methods, system and apparatus of the invention. The physical state of one or more parts of the battery may be correlated to the one or more responsive signals and subsequent quantitative analysis of the collected response signals, and such a correlation may form part of the data set which may be used in evaluating one or more of the to evaluate or predict one or more of (i) state of charge (SOC), (ii) state of health (SOH), and/or (iii) physical state of one or more internal components or parts of a similar battery or the same type of battery. The present inventors have found that sound waves, preferably sound waves generated by an ultrasonic transducer driven at a specific amplitude (voltage) and frequency or a range of amplitudes and frequencies which can be varied to achieve a spectroscopic measurement, most preferably one or more ultrasonic pulses, may be transmitted from at least (and preferably only) one sound source means for transmitting a signal (e.g., a sound wave or sound pulse) through a part of or across the battery, and received by at least (and preferably only) one sound receiver means for receiving a signal from the battery, such a signal includes information representative of the physical state of the battery at its current charge state as the sound wave transits within the battery and its component parts before it is collected by the sound receiver means. Inevitably, the presence of the component parts of the battery, including the cathode and anode at their specific charge level, delays the receipt of the transmitted wave by the sound receiver means. Additionally, the interaction of the transmitted signal with the component parts of the battery also introduces certain distortions in the received signal which differs from the transmitted signal. The received signal may be thus used to generate a waveform which may be digitized and stored in the data storage means and using the processor means, stored as digital data, e.g., the data storage means to provide a datum or data set, from which may be derived one or more of the (i), (ii), and (iii), and/or other physical features, i.e, voltage, current, physical condition of the test battery at the moment of interrogation. This received data signal then, can also be compared to a data set present in the data storage means which has been previously generated by a previously noninvasive interrogation of a different battery of the same type, which itself may be a "reference battery" or which may be a "data set" of another different battery of the same type as the test battery. The waveform and/or correlated information derived from one or more pulse records generated by the noninvasive interrogation of a battery may be compared to this data set to thereby provide an indication of one or more of: (i) SOC and/or (ii) SOH and (iii) physical condition and/or one or more other physical features of the test battery.

The (i) State of Charge (SOC) of a battery may be thought of as the equivalent of fuel gauge for the battery, defining the minimum and maximum charge conditions of the battery at any particular point in time, e.g., 0%=empty or fully discharged, 100%=full, or at maximum charge capacity. It should also be understood that the values, e.g., 0% and 100% may not precisely correspond to the electrochemical limits of the battery, which may be done to protect the battery from excessive charging and/or discharging. When the voltage of the battery is it one of these predetermined voltage limits and no current is being drawn from the battery, the battery is at a known condition or state. During normal operation, batteries are typically not allowed to exceed such limits.

The (ii) State of Health (SOH) of a battery may be thought of the actually measured, or predicted condition of the battery at a particular point in time or over an interval of time, as compared to another battery, and/or to a "reference battery" at a particular point in time, or over an interval of time. The State of Health is in part related to the SOC as a parameter, as typically over the number of repeated charge and discharge cycles the performance of batteries may degrade over time which is reflected in the SOH and in the SOC. A change in the SOH usually occurs over a longer interval or time, or over a longer series of charge/discharge cycles and are often attributed to undesired changes to one or more materials present within the battery over a longer time interval, e.g. intercalation, or other changes. The SOH of the battery may be used to compare the overall performance conditions of a tested battery at a point in time and/or over an interval or time, and/or predict the performance of a tested battery at a future point in time or future interval of time, as compared to another battery and/or reference battery. Determining or predicting the SOH of test battery may be particularly useful in evaluating the current operating characteristics of the test battery as well as evaluating or predicting the future operating characteristics of a test battery as compared to another battery and/or a reference battery. The latter is particularly useful in providing a noninvasive, real-time method for identifying batteries which do not meet designated performance parameters and/or safety parameters when interrogated. Such may also be useful in the identification of batteries which would be likely to fail to meet acceptable predesignated performance characteristics and/or safety parameters at a future.

The (iii) physical state of one or more internal components or parts of the battery under interrogation may be understood as a sudden, usually irreversible, change in the condition of one or more parts of a battery which causes a reduction in the performance of the battery to unacceptable limits (e.g, which may be a partial or total failure of the battery's operation), or which may be indicative of a physical change in the structure of the battery. Such are typically considered to be physical changes which occur within a battery over a relatively short interval of time, including but not limited to: leakage of the sealed battery, delamination of internal battery parts or surfaces, removal of critical surface layers from parts of the battery or mechanical failure, e.g, cracking, of one or more parts of the battery. Such typically cause rapid or immediate breakdown in the operation of the battery, or may otherwise cause or lead to undesired effects such as potential explosion of the battery.

Generally, according to the methods of the invention, a sound signal is transmitted into the battery from one or more one sound source means, preferably is transmitted across the battery and through some or all of the internal components or parts thereof. A responsive sound signal is received from the battery, and collected, by one or more sound receiver means, which responsive sound signal provides information and characteristic data indicative of the operational status of the battery being interrogated in such manner. The sound signal may be any sound signal which may be satisfactorily transmitted into the battery rate, preferably across the battery through the internal component parts thereof. The duration of the sound signal may be a continuous sound signal transmitted for the duration one or more charge/discharge cycles, or the sound signal may be of a shorter duration, e.g, less than one or more charge/discharge cycles. The duration of the sound signal may be very brief, e.g, 1 second or less, preferably 0.5 seconds or less, more preferably 0.1 seconds or less, and particularly preferably 0.01 seconds or less. The sound signal advantageously has a frequency of about 10 Hz or greater, preferably has a frequency in the range of 0.005-50 MHz, and presently preferably is an ultrasonic signal having a frequency in the range of 0.05-50 MHz. Any sound-generating device may be used as a sound source means but preferably is a transducer of appropriate operating characteristics. The sound signal is preferably an ultrasonic pulse or series ultrasonic pulses signal which is/are emitted by the at least one sound source means. The amplitude and the frequency of the sound signal may be programmatically controlled, e.g. by the controller means and/or processor means. As the sound signal passes into the battery and through internal components or parts thereof, a part of the sound signal is transmitted through an internal component thereof, a part of the sound signal is dissipated within the internal component, and a part of the sound signal is reflected from the internal component, particularly at the interface of an internal component and adjacent internal components. These transmitted and/or reflected sound signals are collected by a least one sound receiver means which can be any device which is effective for this purpose. Advantageously, the at least one sound receiver means is a transducer having operating characteristics appropriate for receiving sound signals in the frequency range of 10 Hz or greater, preferably in the range of 0.005-500 MHz, and presently preferably is an ultrasonic signal having a frequency in the range of 0.05-50 MHz. Preferably the at least one sound receiver receives sound signals within the range corresponding to that of the at least one sound source means.

The collected transmitted and/or reflected sound signals and their timing relative to the sound signal transmitted by the sound source means provide information and characteristic data used in ultimately determining one or more of the (i) state of charge (SOC), (ii) state of health (SOH), (iii) physical state of one or more internal components or parts of the battery being interrogated and/or one or more other physical features of the test battery.

This information and characteristic data may be collected over one or more charge and/or discharge cycles of the battery in order to generate a data set representative to the performance characteristics of the battery being interrogated by transmitted sound waves. The information and characteristic data may derived from the collected signal which is received from the battery following transmission of a sound signal; the collected signal may be received either as a signal transmitted through one or more of the internal components of the batteries, at a point distal from a source of the sound signal, and/or as a signal which includes reflection of the transmitted sound signal, at a point proximate to the source of the sound signal. The former requires the use of two separate devices, at least one sound source means which is separate from at least one sound signal receiver means which are affixed to or close proximity to at least two separate parts of the surface of a battery, while the latter permits for the use of a single device which operates as both a sound source means and a sound signal receiver means which may be affixed to or in close proximity to only one part of the surface of the battery.

Figure 2:
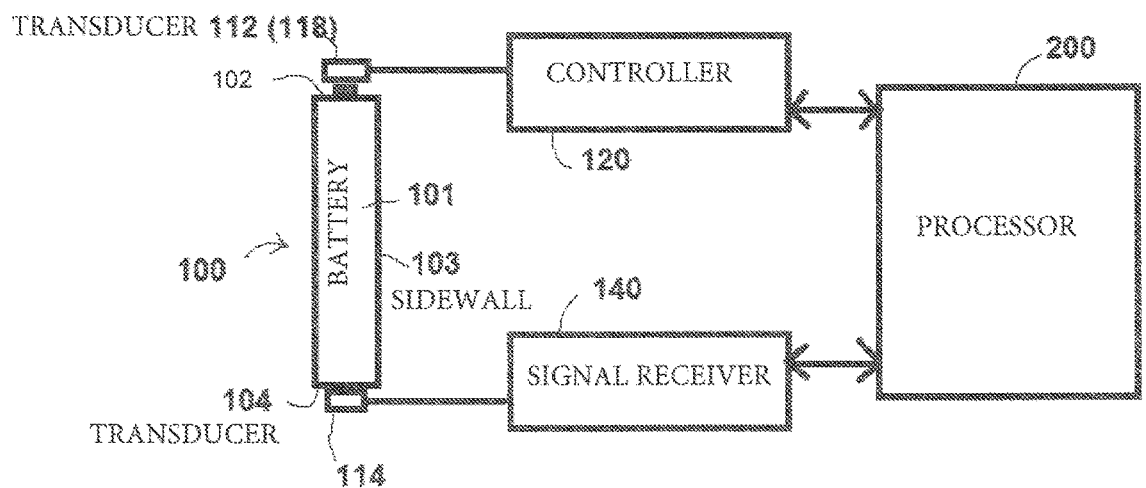
FIG. 2 illustrates a first embodiment of an apparatus according to the invention.

FIG. 2 illustrates an embodiment of an apparatus and a system for interrogating a test battery in order to determine one or more of: (i) its state of charge (SOC), (ii) its state of health (SOH), (iii) physical state of one or more internal components or parts and/or one or more further physical parameters of the test battery. As depicted to a battery 101 (e.g, which may be a conventional 18650 type Li ion battery, prismatic or pouch Li Ion battery, NiCd battery, NiMH battery, NiZn battery, Pb Acid battery, or single-use Zn $MnO_2$ alkaline battery) having at opposite ends two terminals 102 (positive), 104 (negative) and a sidewall 103 is provided to the apparatus 100. In the near proximity of, or attached to the terminals 102 are respectively a transducer 112 which functions as the sound source means, and as the sound signal receiver means a further transducer 114. In FIG. 2 transducer 112 is operatively connected, (e.g, via wires, or other signal transmission means) to a controller means 120 which is used to operate the transducer 112 to operate and transmit one or more sound waves, preferably one or more sound pulses having a specific amplitude and frequency, is transmitted from the sound source and into the battery 101, here from the first terminal 102 towards the second terminal 104. The controller means 120 may be, and desirably is operatively connected to a processor means 200. The collected sound signal transmitted through the battery 101 is received and collected by the further transducer 114, which functions as the sound receiver means, which is operatively connected to a signal receiver means 140, which is also in operative communication with the processor means 200. The signal receiver means 140 may include or be for example, a filter which limits the received frequency of sound signals received from the for the transducer 114, and/or may be an analog-to-digital converter which may operate to convert the signal received by the further transducer 114 into digital data which may be communicated to the processor means 200. In this embodiment the operating characteristics and functions of the controller means 120 and the signal receiver means 140 are separate from one another, but one or both may be controlled by the processor means 200.

Figure 3:
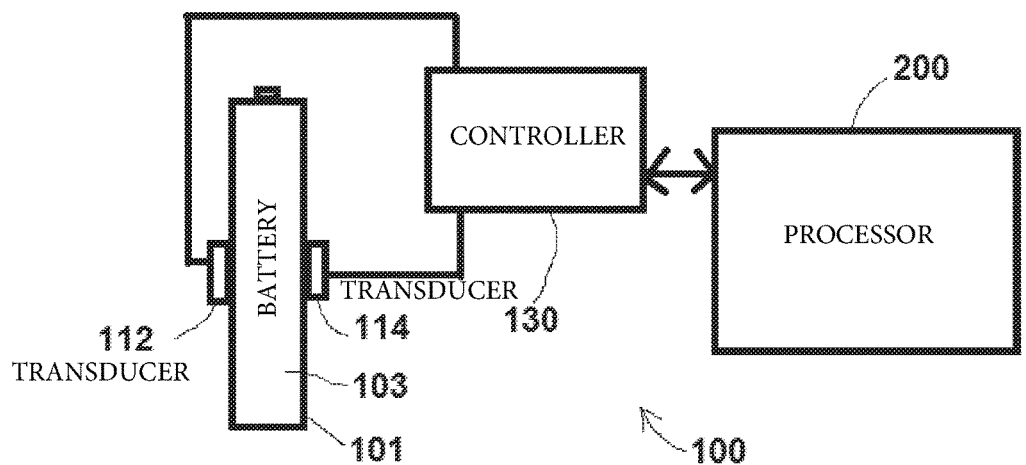
FIG. 3 depicts a second embodiment of an apparatus according to the invention.

FIG. 3 depicts another embodiment of an embodiment of an apparatus and a system for interrogating a battery in order to determine one or more of: (i) its state of charge (SOC), (ii) its state of health (SOH), (iii) physical state of one or more internal components or parts and/or other physical parameters of a tested battery. The present embodiment is primarily distinguished from that of FIG. 2 in that here, the position of the transducers 112, 114 is now transverse relative to the terminals 102, 104 and ends of the battery 101, such that the direction of the sound waves, preferably ultrasonic pulses emanating from the transducer 112 passes through the sidewall 103 of the battery 101 and is received at the transducer 114. Such configuration is particularly useful wherein the internal construction and features of the battery 101 being interrogated by the apparatus and system of the invention is in a "jellyroll" type configuration such that at least one anode layer and at least one cathode layer are parallel to the sidewall 103. Such configuration may for example, be particularly useful in interrogating a wet cell type of battery which has one or more parallel anode and or cathode plates between sidewalls thereof. Further in the present embodiment, the controller means 130 now operatively includes both of the controller means 120 which operates to control the operation of the transducer 112, as well as the signal receiver means 140 which receives signal data from the transducer 114 and provides both functions described as being provided by separate devices with reference to FIG. 2. In the present embodiment, the controller means 130 is also operatively connected, (e.g, via wires, or other signal transmission means) to a processor means 200.

Figure 4:
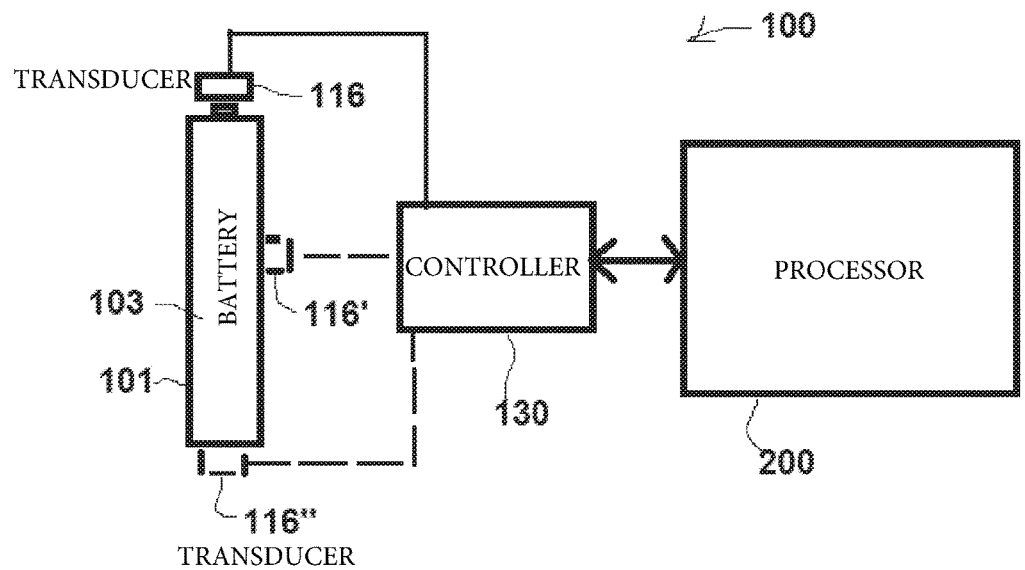
FIG. 4 depicts a third embodiment of an apparatus according to the invention.

FIG. 4 illustrates a further embodiment of an apparatus and a system for interrogating a battery in order to determine one or more of: (i) its state of charge (SOC), (ii) its state of health (SOH), (iii) physical state of one or more internal components or parts and/or other physical parameters of a tested battery. The embodiment of FIG. 4 is similar in many respects in that foregoing FIG. 3 and differs primarily only the fact that that the apparatus and system now includes a single combination transducer 116 which in a single device combines the functions of both prior transducers 112 and 114. In this embodiment the transducer 116 thus is operative to provide both the functions of the sound source means, and of the sound signal receiver means. The transducer 116 is similarly operatively connected to the controller means 130, as has been described more fully with reference to FIG. 3. FIG. 4 also illustrates that the placement of the transducer 116 is positioned adjacent to come on contact with one end of the battery 101, here at the terminal 102. However, as illustrated with the "phantom" representations in dotted line format, the placement of the of the transducer 116 may be placed at the opposite terminal or adjacent thereto such as illustrated by transducer 116" or adjacent to one contact with a sidewall 103 of the battery 101 as represented by transducer 116'. The embodiment of FIG. 4 thus illustrates in an apparatus and a system wherein the combination transducer 116 operates to both transmit sound waves into the battery 101, and to receive reflected sound waves returned from the battery 101. The embodiments of FIGS. 2 and 3, in contrast to that of FIG. 4, illustrate apparatus and a system for interrogating a battery in which transmitted sound waves which is passed through a part of a battery 101. Nonetheless, it is to be understood that the inventive apparatus and a system may also be configured so that sufficient sound source means, and of the sound signal receiver means are present such that the interrogation of the battery utilizes signals from both reflected and transmitted sound waves, as could be easily done wherein, for example with reference to FIG. 4, one or both of transducers 116', 116" were concurrently present with transducer 116.

Figure 5:
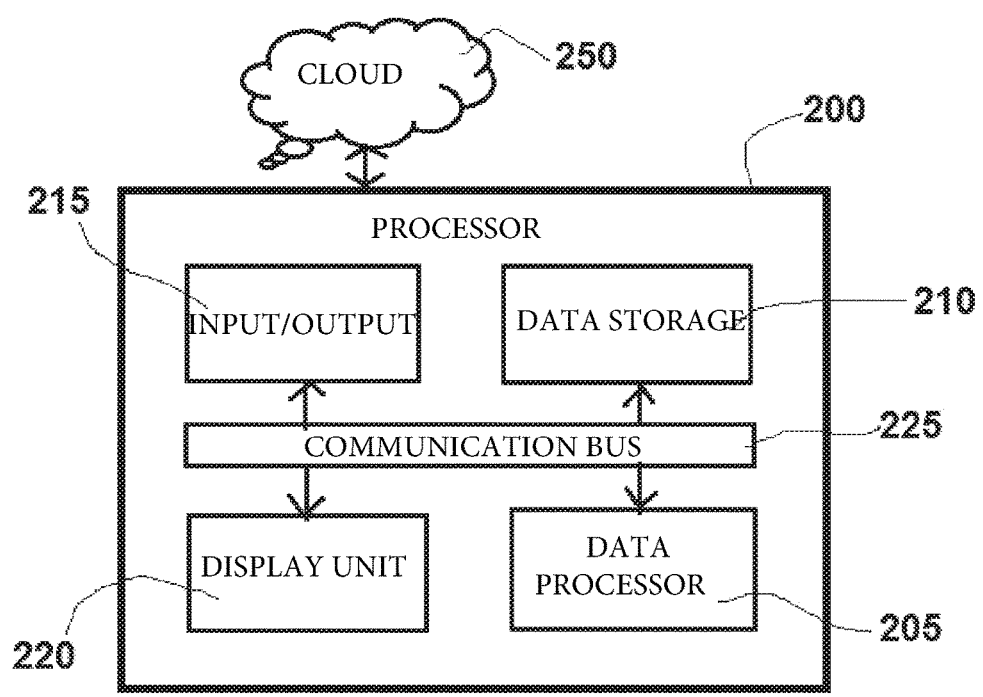
FIG. 5 depicts a part of an apparatus according to the invention.

FIG. 5 depicts a processor means 200. As noted previously, the processor means 200 is operatively connected, (e.g, via wires, or other signal transmission means) to other parts of the apparatus and a system for interrogating a battery of the present invention. The processor means 200 is a nonlimiting example of device which can be used to implement one or more of further operations for determining one or more of the (i) its state of charge (SOC), (ii) its state of health (SOH), (iii) physical state of one or more internal components or parts and/or other physical parameters of a tested battery which is battery is being interrogated or which has been interrogated. Other configurations of a suitable processor means 200 are fully possible, within the scope of this invention, and may differ from that of the depiction of FIG. 5, as other configurations which are suitable for determining one or more of (i), (ii) and/or (iii) from the sound receiver means may also be utilized.

Returning now to FIG. 5, the processor means 200 digital data processing system capable of performing one or more functions of the apparatus and system described herein. The processor means 200 may include a data processor 205, a data storage means 210 and input/output unit 215 and a display unit 220, each of which are in single or bidirectional communication with one another over a common communications bus 225. The processor means 200 need not physically incorporate in its physical construction each of the data processor 205, a data storage means 210, an input/output unit 215 and a display unit 220 as such may be separate physical devices or elements, which need only be functionally interoperative with one another, such as via a common communications bus 225.

The data processor 205 serves to execute instructions for software that can be loaded into either the data processor 205 or other part of the processor means 200, e.g., into a part of the data storage means 210. Such software present may be a series of programs instruction steps for execution by the data processor 205. The data processor 205 can be one or more processors, or may be a multiprocessor core, or may be implemented one or more heterogeneous processor systems. The data processor is however advantageously implemented by a solid state Central Processor Unit (CPU) such as may be found in conventional computer devices, e.g. Intel microprocessor device (e.g., Pentium, Celeron, i3, i5) or AMD microprocessor device (e.g., Athlon, Phenom) with an appropriate control or peripheral chipset mounted on a motherboard. The data processor 205 can be used for operating on data provided from the data storage means 210 and/or from the controller means 120, 130 and/or signal receiver means 140 to derive or determine of one or more of the (i) its state of charge (SOC), (ii) its state of health (SOH), (iii) physical state of one or more internal components or parts of a tested battery and/or other physical parameters of a battery which is being, or has been interrogated. The data processor 205 can be used for operating on data provided from the data storage means 210 and/or from the controller means 120, 130 and/or signal receiver means 140 to derive or determine of one or more of the (i) its state of charge (SOC), (ii) its state of health (SOH), (iii) physical state of one or more internal components or parts of a tested battery and/or other physical parameters of a tested battery which is being, or has been interrogated, relative to a reference battery. Such operations may be controlled by a set of suitable instruction steps, e.g. a computer program, which may also be stored in the processor means 200.

The data storage means 210 may be used to store data provided from the data storage means 210 and/or from the controller means 120, 130 and/or signal receiver means 140 which may be used by the processor means 205 in calculating one or more of the (i) its state of charge (SOC), (ii) its state of health (SOH), (iii) physical state of one or more internal components or parts of a battery and/or other physical parameters of a tested battery. The data storage means 210 may be provided by one or more physical devices or units. The data storage means 210 may also be used to store the output of such calculations performed by the processor means 205. The data storage means 210 may also be used to store one or more instruction steps, or a computer program used by the processor means 205 in its calculations.

The data storage means may be implemented as a random-access memory which one or more components or devices which can be used to store data or instruction steps, e.g, computer program steps for a longer duration of time and include without limitation: hard drives, flash memory, rewritable optical discs, magnetic tape which may optionally be removed from the processor means 200, as well as solid-state memory devices, e.g, RAM, ROM, PROM, EPROM, EEPROM, which typically would form part of the data storage means.

The input/output unit 215 may be one or more devices which provides for the input and output of data with an operator, e.g, a keyboard, mouse, touch sensitive screen, tablet, etc, or with other devices which can be connected to the processor means 200. Such for example, can be use to provide unidirectional and/or bidirectional communication with further functional devices, such as the controller means 120, 130 and/or signal receiver means 140 as described with reference to FIGS. 2, 3 and 4. Such may be used, for example, to transmit commands or control instructions to the controller means 120, 130 and well as to receive information from the signal receiver means 140. The input/output unit 215 may also be used to provide communication links between the processor means 200 and other communications protocols which are external to the processor means 200. For example, the processor means 200 may be in unidirectional and/or bidirectional communication with an external communications network, such as the World Wide Web which may be used to transmit and/or receive information via "the cloud" 250. Such communications protocols may, for example be useful in providing information at a remote location from the apparatus and a system for interrogating a battery. Such may for example cause or prompt a further response or action. For example, under certain operating conditions the processor means 200 may be used to transmit information or data indicative of one or more of the (i) state of charge (SOC), (ii) state of health (SOH), (iii) physical state of a battery, the lattermost (iii) which may be particularly useful in triggering an alarm or providing a warning of an unsafe current operating condition of a battery under interrogation, or predicted unsafe operating condition of a battery which would be expected to occur relative to a data or information relative to the baseline data of the reference battery.

The processor means 200 also includes a display unit 220 through which information representative or indicative of one or more of information or data indicative of one or more of the (i) state of charge (SOC), (ii) state of health (SOH), (iii) physical state of a battery may be presented to an operator (e.g., human operator) or with other devices which may be connected to the processor means 200, or which may form a part thereof. Such a display unit may and visual display monitor or a printer, whereby said information or data indicative of one or more of (i), (ii) and/or (iii) is provided. The display unit 220 may also be used in communicating with and/or controlling, (e.g, triggering) a non-visual device, such as an audible alarm, siren, indicator light, etc., particularly wherein a fault or failure condition of an interrogated battery has occurred, or is expected to occur based upon the information relative to the baseline data of the reference battery.

The processor means 200 also includes a common communications bus 225. The common communications bus 225 may be a single bus or a plurality of buses which provides for communications between two or more of the data processor 205, a data storage means to 10 and input/output unit 215 and a display unit 220. The communications bus 225 may comprise for example an input/output bus, as well as can be implemented using any suitable type architecture that provides for the transfer of information and data between the different components of the processor means 200.

It is to be understood, that with reference to FIG. 5 and the foregoing description that the different components of the processor means 200 are provided by way of illustration and not by way of limitation. It is foreseen that additional components or parts may be additionally included in the systems of the invention, which additional components or parts need not necessarily form a part of the processor means 200. Such may be, for example additional (or remote) memory storage devices which can connected either directly to the communications bus 225, or which can be connected via the input/output unit 215 to the processor means 200. Such may for example, be useful as a data cache or library of one or more battery interrogations performed utilizing the apparatus and method of the present invention. Such an additional memory storage device may be used for example to store a larger amount of data relating to one or more battery interrogations than could be concurrently stored in the data storage means 210; such a library for example may be generated by interrogating a large number of tested batteries. Such a library may be useful, for example, in a quality control operation in which the interrogation results of a tested battery could be compared to data from a large number of previously tested batteries.

In certain embodiments the function of the controller means 120, 103 and/or the signal receiver means 140 may be included the operation of the processor means 200. Such may, by non-limiting example, be achieved by the controlling the operation of one or both of the controller means 120, 103 and/or the signal receiver means 140 via the input/output unit 215.

Other configurations and other architectures may be used for the processor means 200 and its different components other than as has been specifically described herein, and such are also considered to fall within the scope of the present invention.

In a preferred method of the invention, a battery is interrogated utilizing an apparatus as described herein by generation of a "pulse record" wherein, during a charge/discharge cycle of the battery (which may correspond to the change of battery charge between the maximum and minimum values of its SOC), a sound signal, preferably which sound signal is an ultrasonic pulse or is a series of sound signals and particularly preferably is a series of ultrasonic pulses, is transmitted into the battery and one or more received signals from the battery responsive to the one or more transmitted signals are collected by a sound receiver means which is/are then digitized and stored in the data storage means and/or transmitted to the processor. The pulse record of such an interrogation includes the digital data record of the received signal(s), and optionally but preferably also includes further known information regarding the interrogated battery at the time of its interrogation, e.g. one or more of its age, physical condition, its voltage and/or current. A pulse record may be derived from a single received signal during a charge/discharge cycle of the battery, or from a set of received signals which may be intermittently collected during one or more charge/discharge cycles of the battery. For example during a single charge/discharge cycle of the battery the received signal(s) may be sampled on a periodic basis, e.g, for a 0.1-60 second time interval, preferably a 1-15 second time interval during one or more charge/discharge cycles. Alternately a single reading of the received signals may occur during a single charge/discharge cycle. Still alternately received signals may be collected continuously during a one or more charge/discharge cycles of the battery and preferably the received signal(s) is sampled on a periodic basis e.g., 2 or more, 5 or more, 10 or more, and particularly preferably 100 or times more during a single charge/discharge cycle with intervening periods wherein one or more received signals from the battery responsive to the one or more transmitted signals are not collected by the sound receiver, or if collected are not used by the processor means and/or data storage means. From the foregoing, one or more pulse records may be used in a comparison to a reference data set in order to provide an indication of one or more of (i) state of charge (SOC), (ii) state of health (SOH), (iii) physical state of a battery, or prediction of one or more of the (i) state of charge (SOC), (ii) state of health (SOH), (iii) physical state of a battery and/or its predicted future performance.

In a preferred embodiment of a method of the invention for the generation of a reference data set and/or of a data set, a plurality of pulse records are obtained during the interrogation of a battery, and preferably each pulse record includes information at different charge levels within the maximum and minimum values of test battery's SOC. According to this method the interrogation of the battery occurs during a plurality of successive charge/discharge cycles. Preferably at least two, more preferably at least 25, individual pulse records are generated.

In a preferred embodiment the invention, a battery is interrogated utilizing an apparatus is described herein to generate multiple "pulse records", as described above. Preferably a plurality of pulse records are obtained, preferably at different charge levels within the maximum and minimum values of the battery's SOC. Preferably one or more pulse records are obtained within an individual (single) charge/discharge cycle is repeated over two or more, preferably at least five or more, more preferably at least 20 or more successive charge/discharge cycles of the battery under interrogation. From one or more such pulse records, and preferably from a plurality of pulse records can be formed a data set of the characteristics of the test battery, provides a useful record of the (i) its state of charge (SOC), (ii) its state of health (SOH), (iii) physical state of one or more internal components or parts of the test battery and/or one or more further physical conditions of the test battery. Wherein the tested battery is considered to be within acceptable performance limits, then the data set generated, particularly after a number of charge/discharge cycles are provides a useful "data set" which can be used in assessing and analyzing the performance of other, similar batteries or batteries of the same type. Such may also be a "reference data set" if the test battery is considered as meeting desired or required technical performance parameters for the particular battery type and thus be represent a "reference standard" for the particular battery type. The assessment of the data and information received from the one or more pulse records is performed by the processor means 200, which operates to quantitatively analyze using known art analytical methods, e.g., wavelet analysis of vectors, fourier transformation, which are performed using a processor means, which are used to form a data set from the battery being interrogated which may be used to compare with a reference data set or other data set stored in the data storage means. Comparison of the quantitatively analyzed data and information received from the one or more pulse records is performed by a further quantitative analysis by the processor means 200 using known art analytical methods, e.g., comparing a wavelet analysis of vectors between data sets, comparing the fourier transforms between the data sets, by performing a Bayesian analysis of the data sets, which comparison is performed by a processor means. The comparison may be used to determine a degree of difference between the data and information received from the one or more pulse records and with the reference data set or other data set stored in the storage means. Such a comparison may compare all or part of the data in the reference data set or data set with the data and information received from the one or more pulse records of the battery being interrogated. The degree of difference may be quantified, and used to represent designated performance parameters and/or safety parameters within which the interrogated battery is considered to perform acceptably, but outside of which the interrogated battery is considered to perform unacceptably.

While such an assessment and comparison of a battery being interrogated may be performed in real time which provides a real-time assessment of one or more of (i) its state of charge (SOC), (ii) its state of health (SOH), (iii) physical state of one or more internal components or parts, and thus provides a method for noninvasively evaluating one or more of (i), (ii) and (iii) of a battery, such an assessment and comparison of a battery being interrogated may be performed after the battery has been interrogated. In such a process, data and information received from the one or more pulse records collected by the processor means during the interrogation is processed and stored in the data storage means, and after the interrogation of the battery by sound waves, only subsequently is the processor means 200 used to compare and determine a degree of difference between the data and information received from the one or more pulse records from the interrogated battery and with the reference data set or other data set stored in the storage means.

Figure 6:
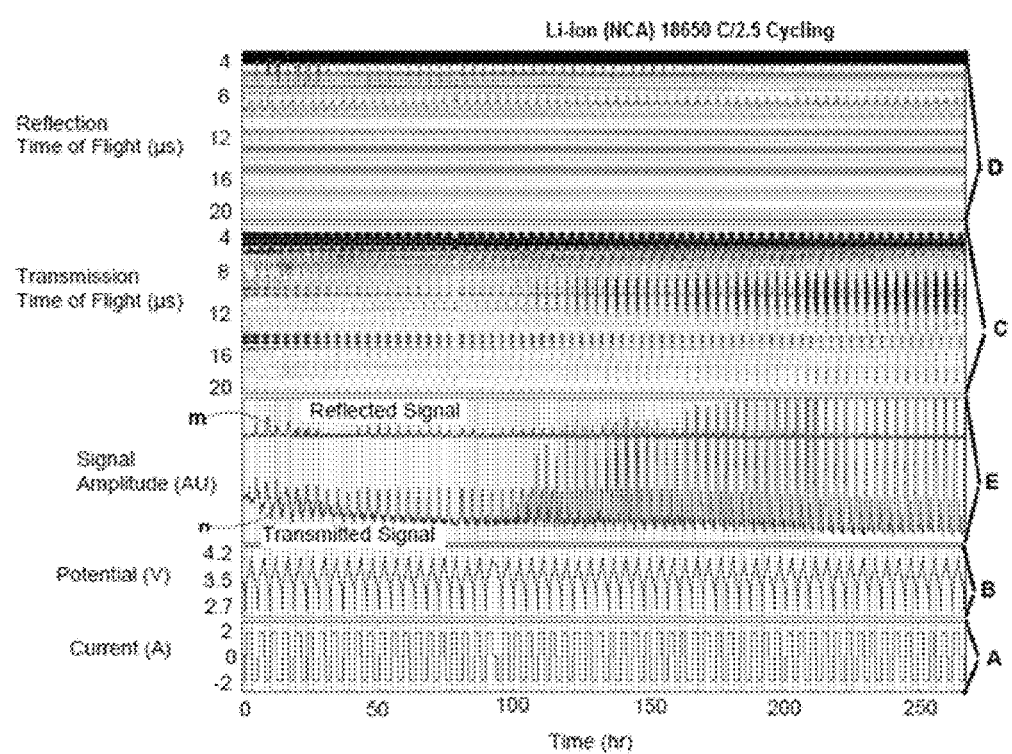
FIG. 6 illustrates a visual representation of a first representative data set.

A visual representation of a representative data set is depicted on FIG. 6. This data set was generated using as the battery a type 18650 cell, (a 'jelly roll" type of NCA/graphite dry cell). The method was performed over a plurality of 34 successive, individual charge/discharge cycles, each having duration of approximately 5.25 hours, and during each individual charge/discharge cycle the current transmitted to and later drained from the battery was controlled in order to provide a positive current approximately 1.3 A for approximately 2.5 hours, then no current was supplied or trained for the battery for a successive 0.25 hours, and then the current was drained from the battery for the remaining 2.5 hours of each charge/discharge cycle. The battery voltage (potential V) was constantly measured, and varied from its minimum (approximately 2.7 V) to its maximum value (approximately 4.2 V). Concurrently throughout the duration of the test, the transducer was operated to transmit a pulse waveform having a driving potential of 400 V and at a frequency of 2.25 MHz into the side of the battery and a second transducer received a responsive signal from the battery, in a configuration as generally described with reference to FIG. 3. As is seen in FIG. 6, the band A indicates the current (A), the band B indicates the voltage (potential) (V). The band C depicts time differences (μs) in the ultrasonic pulse sent by the transducer (the "time of flight") and the receipt of the signal which had been transmitted through the type 18650 cell, and the band D depicts time differences (μs) in the ultrasonic pulse sent by the transducer (the "time of flight") and the receipt of the signal which had been reflected from the type 18650 cell. Band E of FIG. 6 includes two traces, each of the signal amplitude, the upper ("m") being the integrated values at each time interval (0.008 hours) of the data of band D, and the lower ("n") being the integrated value of each time interval (0.008 hours) of the data of band C. As such data, such as is represented on bands C, D and/or E represent useful pulse records, each of which may be correlated to known operating characteristics, e.g., voltage, amperage of the tested battery at any one or more points of time during the interrogation. Such data, whether in an unintegrated data format, e.g, as represented on bands C and D, or whether numerically integrated over specific intervals of time, such as represented on band E of FIG. 6 may be used as a data set, (and when the tested type 18650 cell is considered to be of satisfactory technical performance characteristics for the type 18650 cell, the data set may be a "reference data set"). With such a data set having been established, further type 18650 cells of unknown quality can be tested according to the methods described herein, such that at least one, preferably more than one pulse record is obtained as result of an interrogation of such a further type 18650 cell, and the data derived from such an interrogation can be compared using the processor means 200 of FIG. 5 against one or more data points from the data set (or reference data set, when appropriate) stored in a data storage means 210 accessible by the processor means 200 via the bus 225. The result of such a comparison can be output to the display means 220, or via the input/output means 215 elsewhere, e.g., to "the cloud" 250.

In one embodiment, which is particularly relevant in a manufacturing process for the production of batteries, to ensure a degree of quality control, the input/output means 215 could for example communicate with further automated devices which could remove the tested battery which has been determined by the controller means 200 as failing to meet predesignated performance characteristics of such types of cells (batteries) from the production line, e.g., reject the battery. In such a manufacturing process for batteries, batteries are noninvasively interrogated utilizing a method a described herein to evaluate or predict one or more of one or more of: (i) its state of charge (SOC), (ii) its state of health (SOH), (iii) physical state of one or more internal components or parts during the manufacturing process to ensure that the interrogated battery ("test battery") meets or falls within acceptable performance characteristics for the type of battery. This principle is for example, discussed with reference to FIG. 6A which is a fragment of FIG. 6. During a manufacturing process for batteries, a test battery is noninvasively interrogated, and the received signals from the sound receiver means are processed to by the processor means, and compared to a data set or reference data set for a similar type of battery present in the data storage means. Test batteries which fail to meet acceptable performance characteristics as determined by the processor means are removed from the manufacturing process, and optionally discarded.

Figure 6A:
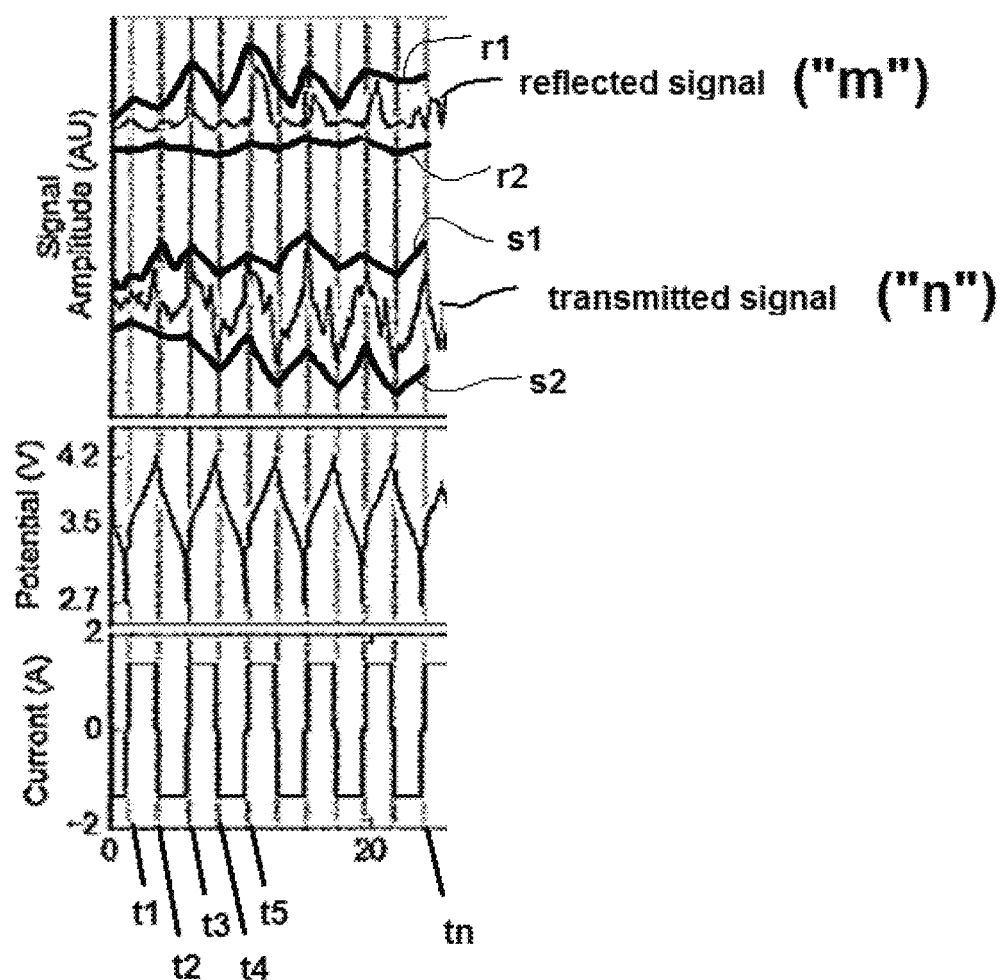
FIG. 6A depicts a fragment of FIG. 6.

As is seen from FIG. 6A, therein are additionally provided adjacent to the reflected signal trace, an upper limit reflected signal trace "r1", and a lower limit reflected signal trace "r2" for a corresponding time interval, e.g, "t1", "t2', "t3", to "tn" which define an envelope of acceptable signal amplitude values for a reflected signal if such a signal value from a tested battery were within t1 and t2 envelope at a specific time. As can also be seen from FIG. 6A there is also provided adjacent to the transmitted time signal trace, an upper limit transmitted signal trace "s1", and a lower limit transmitted signal trace "s2" for a corresponding time interval, e.g, "t1", "t2', "t3", to "tn" which define an envelope of acceptable signal amplitude values for a transmitted signal if such a signal value from a tested battery were within s1 and s2 envelope at a specific time. Thus, according to this illustration, it can be understood that performance characteristics can be established or designated for a particular type of battery which may be derived from the measured performance characteristics of a similar or like type of battery having acceptable performance characteristics, and from which battery had been generated a reference data set using a method according to the invention. In the nonlimiting embodiment discussed with reference to FIG. 6A, the predesignated performance characteristics are disclosed as deviations from the integrated resultant transmitted and/or reflected signal amplitudes at a particular time interval, e.g. t1, t2, . . . tn, as compared to the values derived from the reference data set at a corresponding time interval. Thus, the performance characteristics of a test battery can be determined by the noninvasive method of the invention and compared to that of a reference data set (or, data set) and a comparison made. As part of the comparison, a degree of deviation of the performance characteristics of the test battery may be made with data from a reference data set, and if the deviation is considered to be excessive such provide a present indication, as well as a future prediction that the test battery has unacceptable current technical performance in some respect and/or may expected to exhibit unacceptable technical performance at some time in the future. The degree of deviation may be numerically quantified (e.g., as a percentage deviation, or other quantity), and determined by the data processor of the processor means. Such may be according to known art analytical methods, e.g, comparing a wavelet analysis of vectors between data sets, comparing the fourier transforms between the data sets, by performing a Bayesian analysis of the data sets, which comparison is performed by a processor means, which may be statistically compared for the degree of deviation. The foregoing example of such a comparison by the processor mean is however to be understood as illustrative, but not limiting of this principle and other criterion may be established with respect to determining acceptable predesignated performance characteristics which can be applied when comparing the performance of an interrogated tested battery to that of a reference data set for the same type of battery.

Figure 7A:
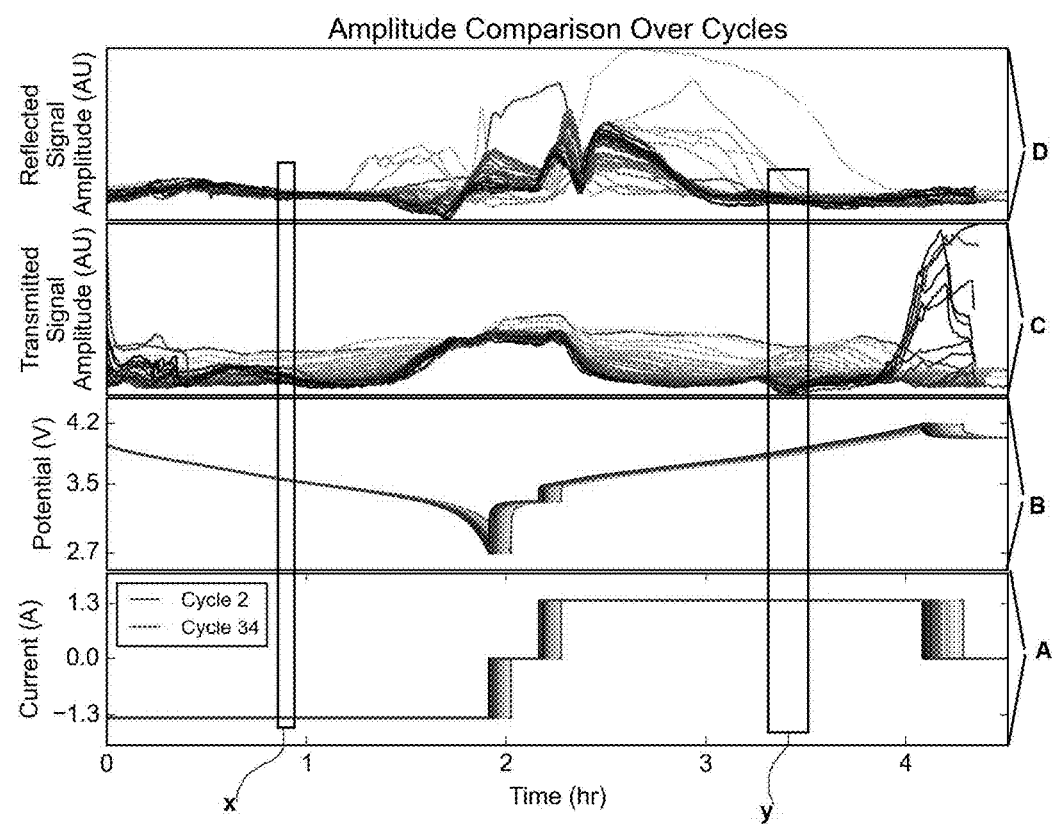
FIGS. 7A and 7B provide alternative depictions of the representation of FIG. 6.
Figure 7B:
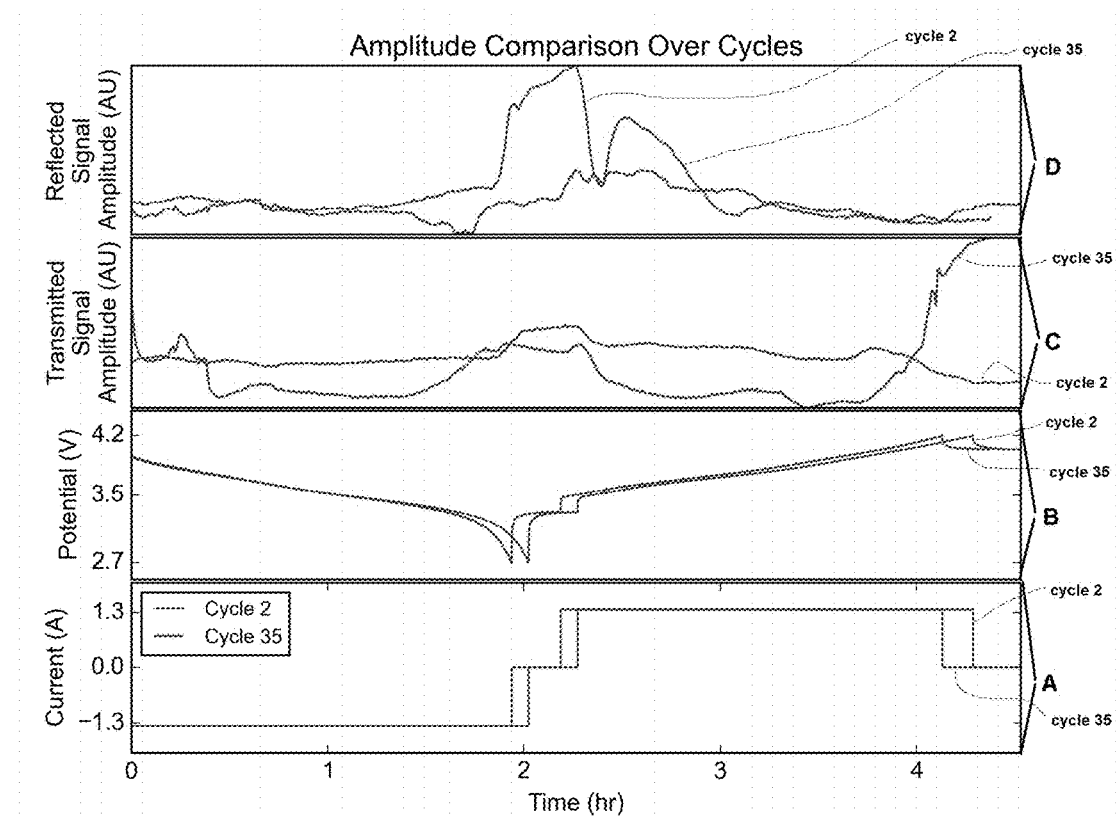

FIGS. 7A and 7B provide in an alternative visual format, the data of FIG. 6. As is firstly noted, the x-axis indicates that the test limits of the represented data are over the time interval of a single charge/discharge cycle, with the depicted data being the representative data of the voltage (potential)) (V) as illustrated on band B, band C depicts time differences (µs) in the ultrasonic pulse sent by the transducer (the "time of flight") and the receipt of the signal which had been transmitted through the type 18650 cell, and the band D depicts time differences (µs) in the ultrasonic pulse sent by the transducer (the "time of flight") and the receipt of the signal which had been reflected from the type 18650 cell. Band A indicates the current being charged or discharged from the battery during the duration of each time interval. Each of bands A, B, C and D include multiple traces representing, respectively; the current, voltage, transmitted signal amplitude and reflected signal amplitude for each of the 34 charge/discharge cycles to during which the the type 18650 cell, (a "jelly roll" type of NCA/graphite dry cell) was interrogated in the manner previously described with reference to FIG. 6. As is seen therefrom, while the waveforms of the current and voltage (potential) were generally consistent, a noticeable shift in each is manifested between an early charge/discharge cycle, "cycle 2" and the final charge/discharge cycle, "cycle 34" of the interrogation. Such is more clearly understood from FIG. 7B which depicts only a limited set of data corresponding to only these two cycles. Thus the representations of FIG. 7A provides a "cumulative overlay" of the current, voltage, transmitted signal amplitude and reflected signal amplitude over 34 successive charge/discharge cycles, with FIG. 7B being a subset of the cumulative overlay.

The represented data may be used to further illustrate the inventive method of predicting the State of Charge (SOC) from one or both of the transmitted signal amplitude based on the time differences (µs) in the ultrasonic pulse sent by the transducer (the "time of flight") and the receipt of the signal which had been transmitted through battery (band C) and the reflected signal amplitude on the time differences (µs) in the ultrasonic pulse sent by the transducer (the "time of flight") and the receipt of the signal which had been reflected from the battery (band D). Where the data represented on FIG. 7A is present as a data set in a data storage means data, e.g, as a reference data set for a previously tested type 18650 cell (battery), the apparatus of the invention may be used to interrogate a further test battery in order to determine the SOC and/or the SOH of the test battery. Accordingly a test battery is interrogated according to a method as described herein, and the resultant information and data relating to the collected signal received from the battery is processed by the processor means 200 and compared to the corresponding data set in the data storage means. By way of nonlimiting example, there are also depicted two correlation zones "x" and "y", which may be used to demonstrate the correlations between the stored data set and the information and data from the interrogated test battery. With reference first to correlation zone "x", if the processor means 200 determines that the information and data of the transmitted signal amplitude based on the time differences (µs) and/or (but preferably both) the reflected signal amplitude on the time differences (µs) fall within or near to the traces within zone "x", the voltage (potential) and/or current (A) may be correlated or predicted to be within the range also falling within correlation zone "x", viz., approximately 3.6 v and −1.3 (A). With reference data the second correlation zone "y", if the processor means 200 determines that the information and data of the transmitted signal amplitude based on the time differences (µs) and/or (but preferably both) the reflected signal amplitude on the time differences (µs) fall within or near to the traces within zone "y", the voltage (potential) and/or current (A) may be correlated or predicted to be within the range also falling within correlation zone "y", viz., approximately 4.0 v and +1.3 (A). Thus a noninvasive evaluation of the SOC and the SOH of the test battery may be performed. In the method, electrical contact with the test battery is not required.

Figure 8:
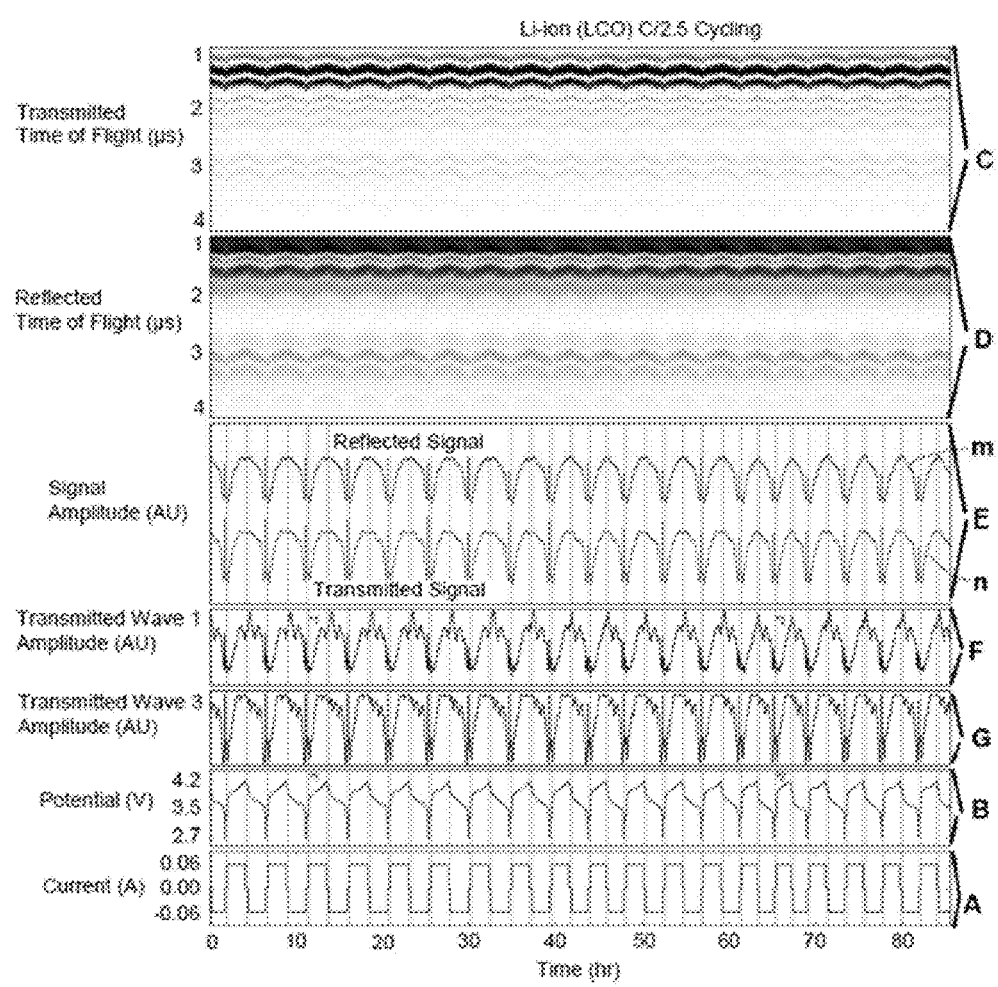
FIG. 8 illustrates a visual representation of a second representative data set
Figure 8A:
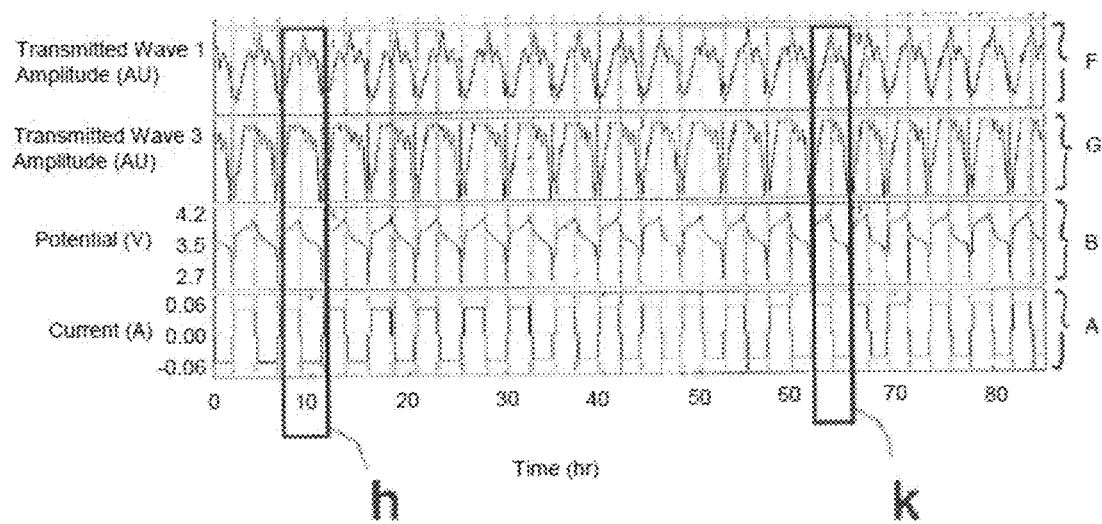
FIG. 8A depicts a fragment of FIG. 8.

FIG. 8 depicts a visual representation of a data set generated from a noninvasive method of an interrogated LiCO$_2$/graphite pouch cell. As is seen from FIG. 8, including as is seen in FIG. 6, the band A indicates the current (A), the band B indicates the voltage (potential)) (V). The band C depicts time differences (µs) in the ultrasonic pulse sent by the transducer (the "time of flight") and the receipt of the signal which had been transmitted through the prismatic cell, and the band D depicts time differences (µs) in the ultrasonic pulse sent by the transducer (the "time of flight") and the receipt of the signal which had been reflected from the prismatic cell. Band E of FIG. 8 includes two traces, each of the signal amplitude, the upper being the integrated values at each time interval (0.008 hours) of the data of Band D, and the lower being the integrated value of each time interval (0.008 hours) of the data of Band C. Band F illustrates a further signal trace, that of first transmitted wave 1 which is obtained from a digital ultrasonic pulser receiver, and whose integrated values at each of the timer intervals is depicted. Band G illustrates a yet further signal trace, that of second transmitted wave 3 which is obtained from a digital ultrasonic pulser receiver, and whose integrated values at each of the timer intervals is depicted. Such data and information which is derived from the interrogation method and as is represented on bands C, D, E, F and/or G represent useful pulse records, each of which may be correlated to known operating characteristics, e.g., voltage, amperage of the tested battery at any one or more points of time during the interrogation. Additionally data from one or more of bands C, D, E, F and/or G and particularly, from one or both of bands F and G provide useful information and data which may be used to also determine and/or predict the SOC and the SOH of the battery evaluated in the test, or of a further test battery of the same battery type, as is generally discussed with reference to FIGS. 8, 8A. Additionally data from one or more of data from one or more of bands C, D, E, and particularly from one or both of bands F and G provide useful information and data which may be used to also determine and/or predict the SOC and the SOH and additionally provide date relevant to the (iii) physical state of one or more internal components or parts. This principle is better understood from FIG. 8A which is an excerpt of FIG. 8. As is there illustrated, the configuration of the waveform within bands F at an early charge/recharge cycle occurring within the first 12 hours of evaluation of the test battery is depicted in the frame "h". The waveform configuration within band F at a later charge/recharge cycle which occurred at approximately 62-64 hours from the start of the evaluation of the test batteries is depicted in frame "k". As can be seen, the waveforms within the frames "h" and "k" at band F display different shapes, which suggests a change in one or more of the parts from which the battery is constructed. The impact of this change is correlated to the change in the voltage potential as depicted in band B which is also within frames h, k. As is visible therefrom, a degradation in the SOC is correlated to the change in the waveform within band F. The change in the waveform provides data and information which can be used by the processor means 200 to compare the performance of the battery over at least one, but preferably over two or more different charge/discharge cycles, and the change in waveform can be used in a determination or prediction of a change in the SOC, SOH and/or the (iii) physical state of one or more internal components or parts. Such a comparison may be according to known art analytical methods, e.g, comparing a wavelet analysis of vectors between data sets, comparing the fourier transforms between the data sets, by performing a Bayesian analysis of the data sets, which comparison is performed by a processor means, which may be statistically compared for the degree of deviation. Such is particularly useful wherein the test battery is of the rechargeable type, and is being continuously or periodically interrogated according to a method and/or work is an apparatus as described herein. Thus during its operation, a noninvasive evaluation of the rechargeable battery can be made, in real time, and wherein the processor means 200 identifies a change in one or more of the data as may be represented within bands C, D, E, and particularly from one or both of bands F and/G and identifies such a change as being relevant to and beyond an acceptable degree of change in one or more of the SOC, SOH and/or the (iii) physical state of one or more internal components or parts of the battery. Such may then cause the processor means 200 to respond in a suitable manner, e.g. by setting an alarm condition wherein a fault or failure condition of a the interrogated battery has occurred, or is expected to occur.

Any of the apparatus and methods of the invention as described herein may be utilized in conjunction with single use type batteries, or maybe use with rechargeable type batteries. Particularly useful in the latter, a more comprehensive data set is available from the application of the methods of the invention upon batteries which are useful over a plurality of charge/discharge cycles.

The apparatus and methods of the present invention are particularly adapted to be used in methods for evaluating one or more of the SOC, SOH and/or the (iii) physical state of one or more internal components or parts of the battery wherein the battery may be evaluated in situ at its place of installation and/or use. Such an in situ or in operando undertaking, without requiring removal of the battery from the device (vehicle) in which it is located, e.g, in a battery compartment of an electrical and/or electronic device, in a vehicle, etc. Any of the apparatus, particularly anyone of the embodiments according to one or more of FIGS. 1-5 may be incorporated into the construction of a device, or vehicle which contains one or more batteries. For example, a cell phone may be constructed which includes one or more transducers which the positions in contact with, or adjacent to one or more parts of a battery installed within the cell phone. The cell phone may include a processor means, and data storage means which, the former of which is operated according to an instruction set or sequence of instructions steps, viz., a computer program, and a data storage means which can be used to store information and data relevant to one or more collected signals, which may include a data set or reference data set relevance to the type of battery present within the cell phone. A method of the invention can be practiced concurrently with the normal use of the cell phone by its owner/operator whereby periodically or continuously the method is performed in order to evaluate one or more of the (i) state of charge (SOC), (ii) state of health (SOH), (iii) physical state of one or more internal components or parts of the test battery and/or other physical conditions of the tested battery as the method of the invention is practiced in a noninvasive manner. In a similar manner, other electrical or electronic devices (e.g. computers, computer tablets, other data communication devices, other portable electronic devices, toys, vehicles such as automobiles, aircraft, etc.) may include a similar construction as described with reference to cell phones herein, and which methods of the invention may be practiced in a continuous manner, or in an intermittent matter in order to evaluate one or more of the (i) state of charge (SOC), (ii) state of health (SOH), (iii) physical state of one or more internal components or parts of the test battery and/or other physical conditions of the tested battery.

Certain aspects of the invention are further disclosed in one or more of the following Examples:

Examples

A number of different batteries were obtained and used in testing. Such batteries included (1) several Zn—MnO$_2$alkaline type AA cells (e.g. Duracell and e.g. CVS) (2) several cylindrical type 18650 batteries based on lithium ion chemistries (LiCoO$_2$ and Li(NiCoAl)O$_2$), (3) a cylindrical type 18650 graphite battery, and (4) a LiCoO2/graphite cell of a prismatic form factor.

An Olympus EPOCH 600 ultrasonic pulser-receiver was used with two 2.25 MHz transducers, in both pulse-echo (reflection) mode and transmission mode. This allowed the measurement of reflected and transmitted signals through the battery. The transducers were held in place with light pressure using a nonconductive plastic holder and a small amount of glycerin was present between the transducer(s) surface and the battery which was used to ensure a reliable acoustic interface between the transducers and the battery. No modifications were made to the cells and they were used as supplied from their respective supplier. The ultrasonic pulser-receiver was controlled to apply ultrasonic pulse of 2.25 MHz, which had a pulse duration of 50 ns, and the pulse was transmitted every 2.5 ms. Concurrently each of the batteries was electrochemically cycled using a Neware BTS-3000 cycler. Conventional galvanostatic protocols were used, a single discharge at C/20, C/10 and C/5 was used for the alkaline AA cells, and a C/2.5 rate was used for the lithium ion batteries. The Neware was time synchronized with the EPOCH 600 ultrasonic pulser-receiver. The collected signal received from the battery was measured every 15 seconds, and the information and data from the ultrasonic pulser-receiver were supplied to a programmed general purpose computer which was suitably programmed to collect and analyze the information and data supplied. Within the computer, the said the information and data supplied was analyzed and a data set or reference data set was provided to data storage means, which could be used for later comparison by the processor means of the computer with a further noninvasive interrogation method of a test battery of the same type as that of the data set present within the data storage means in order to evaluate one or more of one or more of the: (i) state of charge (SOC), (ii) state of health (SOH), (iii) physical state of one or more internal components or parts of the test battery.

FIGS. 6, 6A, 7A and 7B illustrate the derived data and information obtained from an evaluation of a NCA/graphite dry cell type 18650 cell, (a 'jelly roll" type of dry cell having a wound construction) in accordance with the steps of the described experimental method described supra.

FIG. 8 illustrates the derived data and information obtained from the evaluation of a LiCO$_2$/graphite prismatic cell in accordance with the steps of the described experimental method described supra. In the figure, Band E includes two traces, each of the signal amplitude, the upper ('n") being the integrated (normalized) values at each time interval (0.008 hours) of the data of Band D ("Reflected Signal"), and the lower ("m") being the integrated value of each time interval (0.008 hours) of the data of Band E ("Transmitted Signal").

Figure 9:
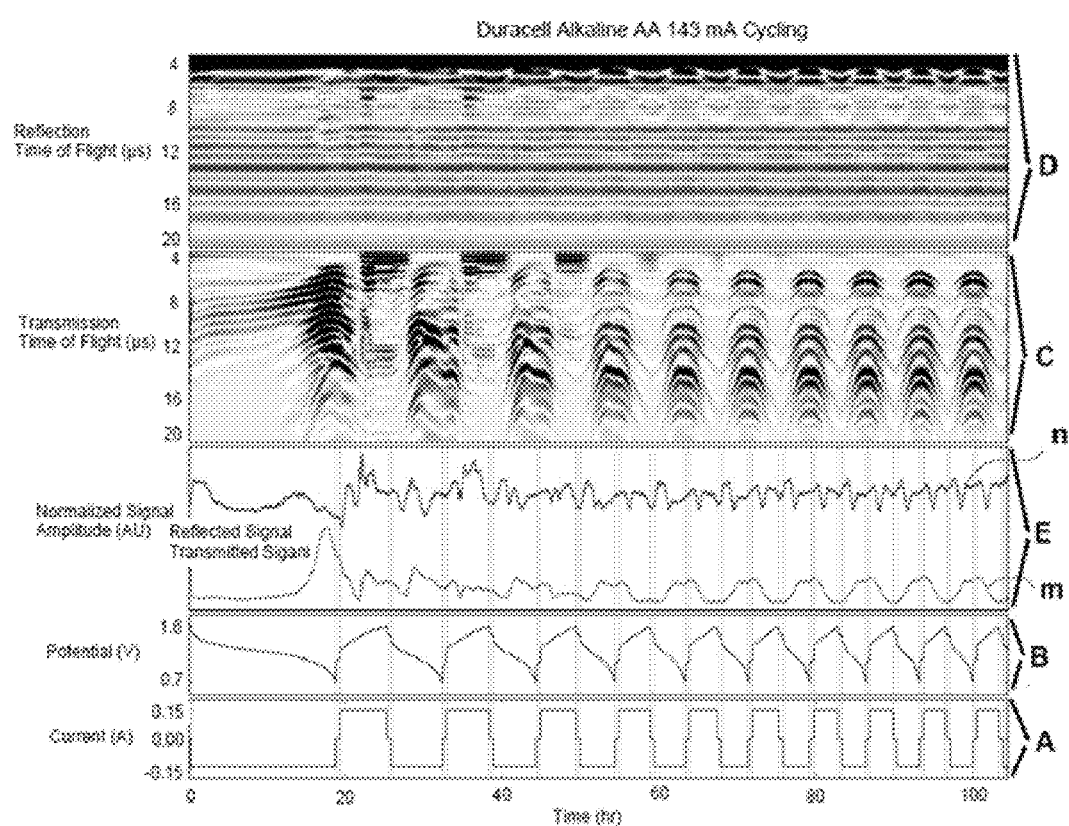
FIG. 9 illustrates a visual representation of a further representative data set.
Figure 10:
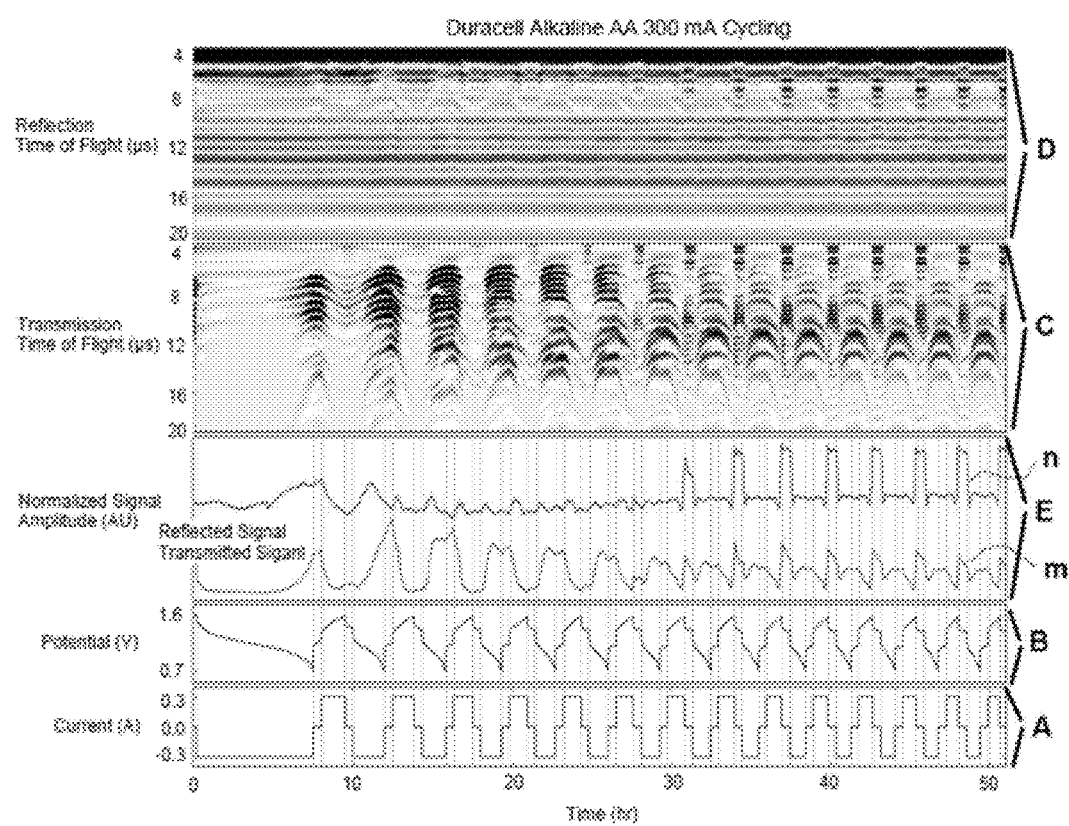
FIG. 10 depicts a visual representation of a further representative data set.

FIG. 9 depicts a derived data set and information obtained from the evaluation of a Duracell Alkaline AA battery of a zinc-manganese dioxide (Zn—MnO2), ("test battery") in accordance with the steps generally described supra. In the analysis, the test battery was cycled as indicated and the current was 143 mA. In FIG. 9, the x-axis indicates the duration of the test in hours, the band A indicates the current (A), the band B indicates the voltage (potential)) (V). The band C depicts time differences (μs) in the ultrasonic pulse transmitted by the transducer (the "time of flight") and the receipt of the signal which had been transmitted through the prismatic cell, and the band D depicts time differences (μs) in the ultrasonic pulse sent by the transducer (the "time of flight") and the receipt of the signal which had been reflected from the prismatic cell. Band E of FIG. 9 includes two traces, each of the signal amplitude, the upper ('n") being the integrated values at each time interval (0.008 hours) of the data of Band D ("Reflected Signal"), and the lower ("m") being the integrated value of each time interval (0.008 hours) of the data of Band C ("Transmitted Signal"). Such data and information which is derived from the interrogation method and as is represented on bands C, D, and/or G represent useful pulse records, each of which may be correlated to known operating characteristics, e.g., voltage, amperage of the tested battery at any one or more points of time during the interrogation. Additionally data from one or more of bands C, D, and/or E and particularly traces n, m provide useful information and data which may be used by a processor means to also determine and/or predict the SOC and the SOH of the battery evaluated in the test, e.g. by comparison with a reference data set, or of a further test battery of the same battery type. FIG. 10 depicts a derived data set and information obtained from the evaluation of a Duracell Alkaline AA battery of a chemistry type zinc-manganese dioxide (Zn—MnO2), ("test battery") in accordance with the steps generally described supra. In the analysis, the test battery was cycled as indicated and the current was 300 mA. Similarly as has been described with reference to FIG. 9, in FIG. 10, the x-axis indicates the duration of the test in hours, band A indicates the current (A), band B indicates the voltage (potential)) (V), band C depicts time differences ($\mu s$) in the ultrasonic pulse transmitted by the transducer (the "time of flight") and the receipt of the signal which had been transmitted through the prismatic cell, and the band D depicts time differences ($\mu s$) in the ultrasonic pulse sent by the transducer (the "time of flight") and the receipt of the signal which had been reflected from the prismatic cell. Band E of FIG. 10 includes two traces, each of the signal amplitude, the upper ('n') being the integrated values at each time interval (0.008 hours) of the data of Band D ("Reflected Signal"), and the lower ("m") being the integrated value of each time interval (0.008 hours) of the data of Band C ("Transmitted Signal"). Again, such data and information which is derived from the interrogation method and as is represented on bands C, D, and/or G represent useful pulse records, each of which may be correlated to known operating characteristics, e.g., voltage, amperage of the tested battery at any one or more points of time during the interrogation. Additionally data from one or more of bands C, D, and/or E and particularly traces n, m provide useful information and data which may be used by a processor means to also determine and/or predict the SOC and the SOH of the battery evaluated in the test, e.g. by comparison with a reference data set, or of a further test battery of the same battery type.

Figure 11:
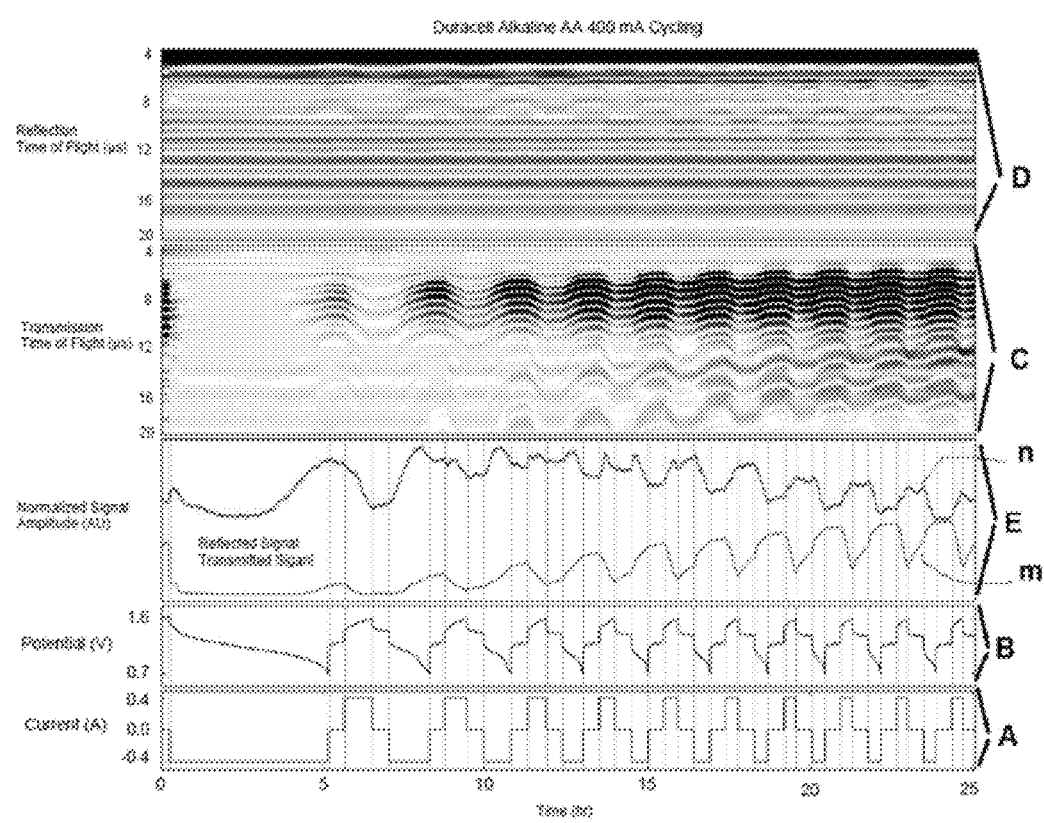
FIG. 11 depicts a visual representation of a further representative data set.

FIG. 11 depicts a derived data set and information obtained from the evaluation of a Duracell Alkaline AA battery of a chemistry type zinc-manganese dioxide (Zn—MnO2), ("test battery") in accordance with the steps generally described supra. In the analysis, the test battery was cycled as indicated and the current was 300 mA. Similarly as has been described with reference to FIG. 9, in FIG. 11, the x-axis indicates the duration of the test in hours, band A indicates the current (A), band B indicates the voltage (potential)) (V), band C depicts time differences ($\mu s$) in the ultrasonic pulse transmitted by the transducer (the "time of flight") and the receipt of the signal which had been transmitted through the prismatic cell, and the band D depicts time differences ($\mu s$) in the ultrasonic pulse sent by the transducer (the "time of flight") and the receipt of the signal which had been reflected from the prismatic cell. Band E of FIG. 11 includes two traces, each of the signal amplitude, the upper ('n') being the integrated values at each time interval (0.008 hours) of the data of Band D ("Reflected Signal"), and the lower ("m") being the integrated value of each time interval (0.008 hours) of the data of Band C ("Transmitted Signal"). Again, such data and information which is derived from the interrogation method and as is represented on bands C, D, and/or G represent useful pulse records, each of which may be correlated to known operating characteristics, e.g., voltage, amperage of the tested battery at any one or more points of time during the interrogation. Additionally data from one or more of bands C, D, and/or E and particularly traces n, m provide useful information and data which may be used by a processor means to also determine and/or predict the SOC and the SOH of the battery evaluated in the test, e.g. by comparison with a reference data set, or of a further test battery of the same battery type.

As can be understood from a consideration of FIGS. 9, 10 and 11, all of which were performed on the same battery type, but at different cycling parameters, the performance characteristics of the interrogated test battery were observed to vary over time, and were influenced by the specific test parameters, viz., current. As can also be understood, data represented on FIGS. 9, 10 and 11 provided a representative "fingerprint" for the specific battery type tested at the various test conditions. Such a fingerprint may be used, for example, in identifying a battery of unknown type by subjecting that battery according to a method disclosed herein, and comparing its performance characteristics with one or more "fingerprints" to determine if the interrogated battery of unknown type exhibits similar performance characteristics.

Figure 12:
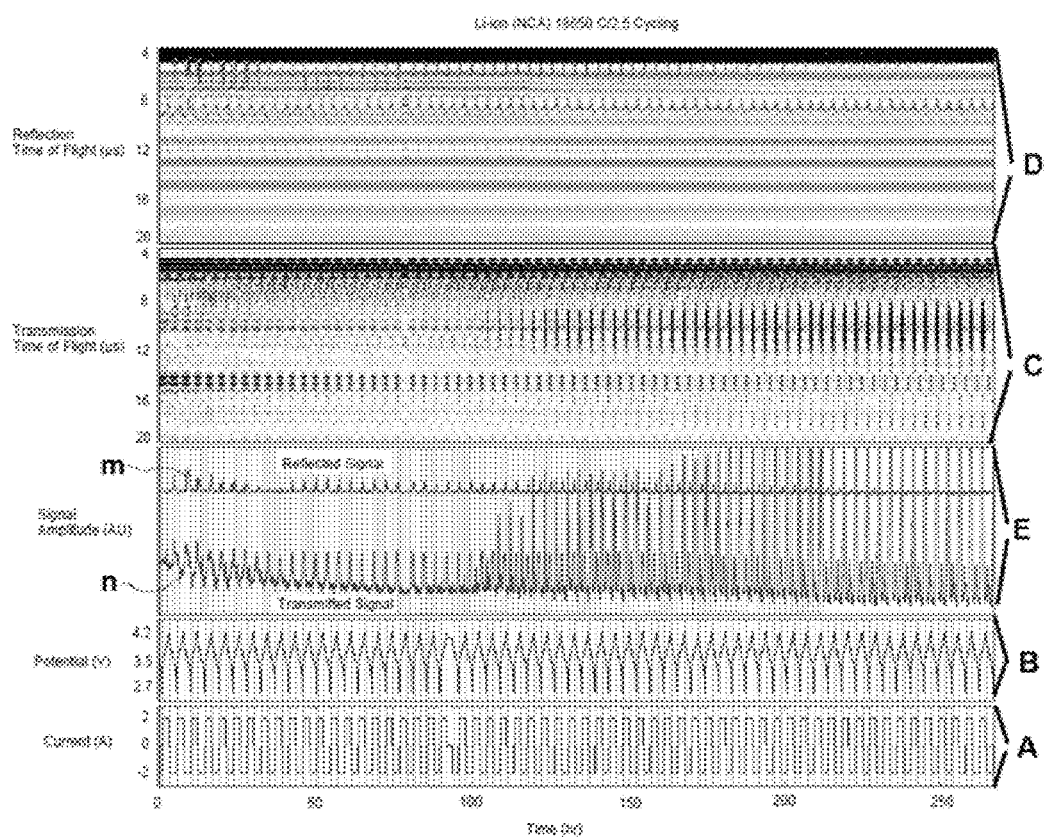
FIG. 12 illustrates a visual representation of a further representative data set.

FIG. 12 provides visual representation of a representative data set generated using as the battery a type 18650 cell, (a "jelly roll" configuration) of a Li-ion (NCA) battery. The method was performed over a plurality of successive, individual charge/discharge cycles, each having duration of approximately 5.25 hours, and during each individual charge/discharge cycle the current transmitted to and later drained from the battery was controlled in order to provide a positive current of approximately 1.3 A for approximately 2.5 hours, then no current was supplied to or drained from the battery for a successive 0.25 hours, and then the current was drained from the battery for the remaining 2.5 hours of each charge/discharge cycle. The battery voltage (potential V) was constantly measured, and varied from its minimum (approximately 2.7 V) to its maximum value (approximately 4.2 V). Concurrently throughout the duration of the test, the transducer was operated to transmit a pulse waveform having a driving potential of 400 V and at a frequency of 2.25 MHz into the side of the battery and a second transducer received a responsive signal from the battery, in a configuration as generally described with reference to FIG. 3. As is seen in FIG. 12, the band A indicates the current (A), the band B indicates the voltage (potential) (V). The band C depicts time differences ($\mu s$) in the ultrasonic pulse sent by the transducer (the "time of flight") and the receipt of the signal which had been transmitted through the type 18650 cell, and the band D depicts time differences ($\mu s$) in the ultrasonic pulse sent by the transducer (the "time of flight") and the receipt of the signal which had been reflected from the type 18650 cell. Band E includes two traces, each of the signal amplitude, the upper ("m") being the integrated values at each time interval (0.008 hours) of the data of Band D ("Reflected Signal"), and the lower ("n") being the integrated value of each time interval (0.008 hours) of the data of Band C ("Transmitted Signal"). As such data, such as is represented on bands C, D and/or E represent useful pulse records, each of which may be correlated to known operating characteristics, e.g., voltage, amperage of the tested battery at any one or more points of time during the interrogation. Such data, whether in an unintegrated data format, e.g, as represented on bands C and D, or whether numerically integrated over specific intervals of time, such as represented on band E of FIG. 12 may be used as a data set, (and when the tested type 18650 cell is considered to be of satisfactory technical performance characteristics for the type 18650 cell, the data set may be a "reference data set"). With such a data set having been established, further type 18650 cells of unknown quality can be tested according to the methods described herein, such that at least one, preferably more than one pulse record is obtained as result of an interrogation of such a further type 18650 cell, and the data derived from such an interrogation can be compared using the processor means 200 of FIG. 5 against one or more data points from the data set (or reference data set, when appropriate) stored in a data storage means 210 accessible by the processor means 200 via the bus 225. The result of such a comparison can be output to the display means 220, or via the input/output means 215 elsewhere, e.g., to "the cloud" 250. In one embodiment, which is particularly relevant, in a manufacturing process for the production of batteries, to ensure a degree of quality control, the input/output means 215 could for example communicate with further automated devices which could remove the tested battery which has been determined by the controller means 200 as failing to meet predesignated performance characteristics of such types of cells (batteries) from the production line, e.g., reject the battery.

Figure 13:
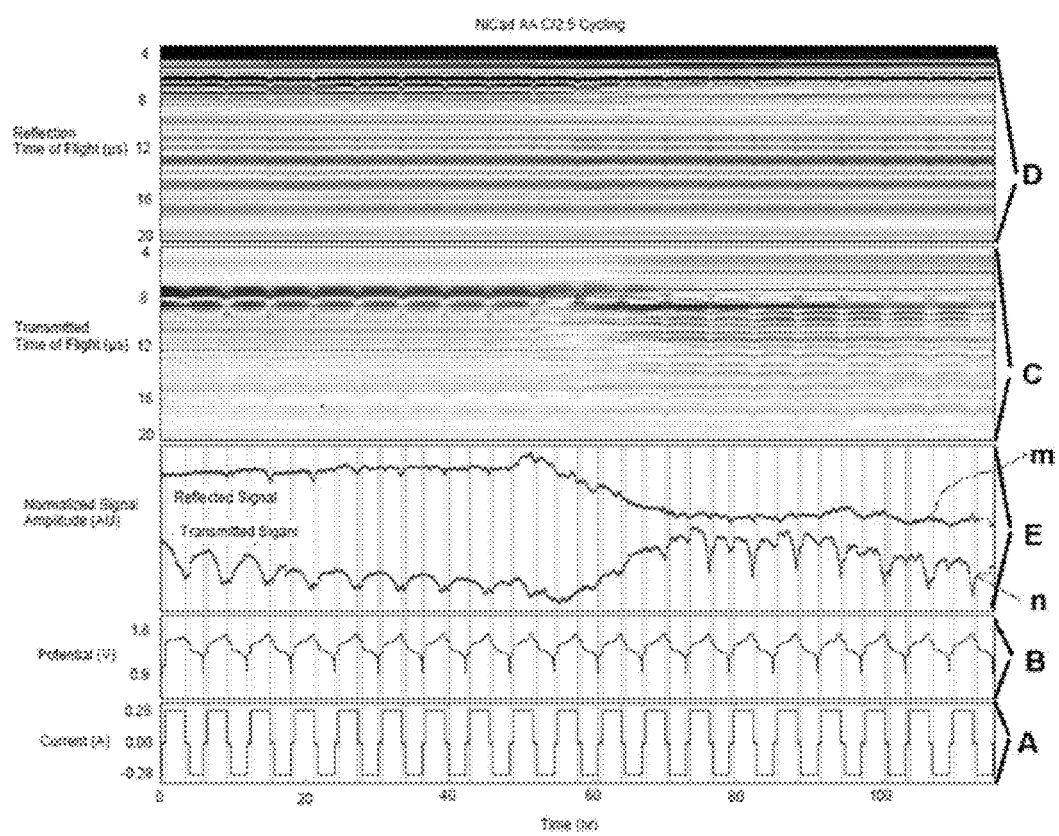
FIG. 13 depicts a visual representation of a yet further representative data set.

FIG. 13 depicts a depicts a derived data set and information obtained from the evaluation of a NiCd battery ("test battery") in accordance with the steps generally described supra. In the analysis, the test battery was cycled at C/2.5 and the x-axis indicates the duration of the test in hours. Band A indicates the current (A), band B indicates the voltage (potential)) (V), band C depicts time differences (μs) in the ultrasonic pulse transmitted by the transducer (the "time of flight") and the receipt of the signal which had been transmitted through the test battery, and the band D depicts time differences (μs) in the ultrasonic pulse sent by the transducer (the "time of flight") and the receipt of the signal which had been reflected from the test battery. Band E includes two traces, each of the signal amplitude, the upper ('m") being the integrated (normalized) values at each time interval (0.008 hours) of the data of band D ("Reflected Signal"), and the lower ("n") being the integrated (normalized) value of each time interval (0.008 hours) of the data of band C ('transmitted signal"). Again, such data and information which is derived from the interrogation method and as is represented on bands C, D, and/or E represent useful pulse records, each of which may be correlated to known operating characteristics, e.g., voltage, amperage of the tested battery at any one or more points of time during the interrogation. Additionally data from one or more of bands C, D, and/or E and particularly traces n, m provide useful information and data which may be used by a processor means to also determine and/or predict the SOC and the SOH of the battery evaluated in the test, e.g. by comparison with a reference data set, or of a further test battery of the same battery type.

Figure 14:
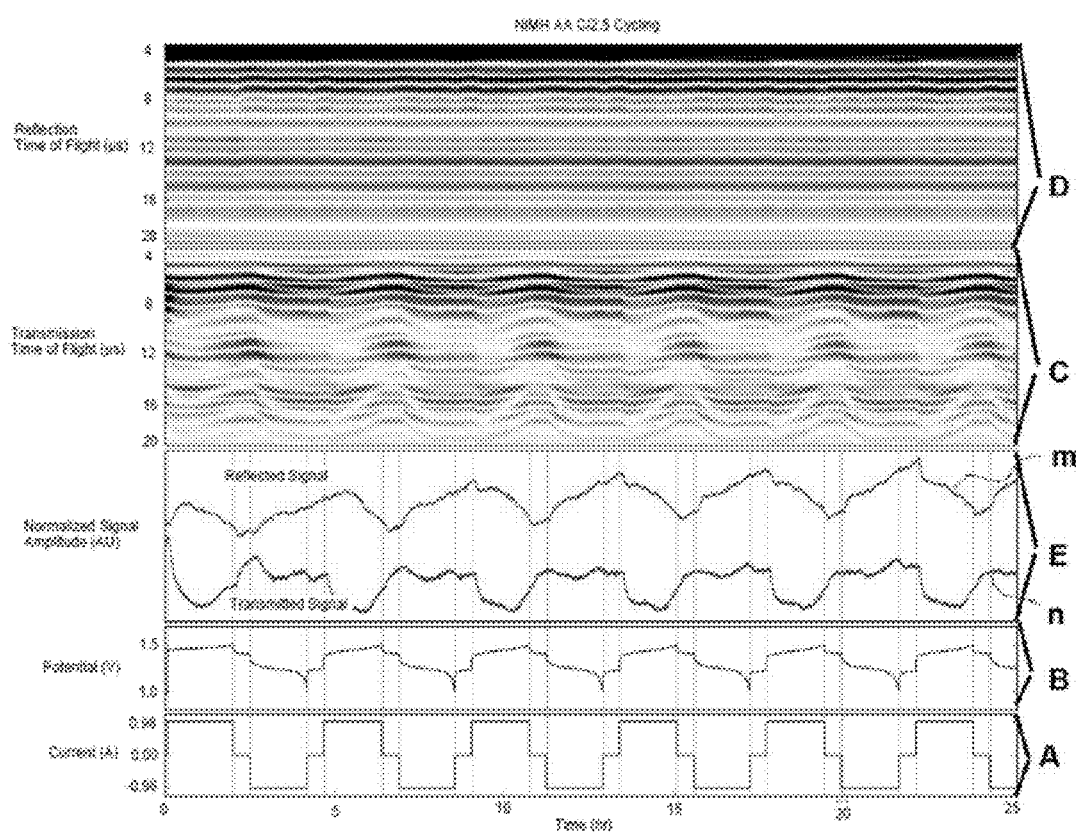
FIG. 14 illustrates a visual representation of a still further representative data set.

FIG. 14 depicts a depicts a derived data set and information obtained from the evaluation of a NiMH AA battery ("test battery") in accordance with the steps generally described supra. In the analysis, the test battery was cycled at C/2.5 and the x-axis indicates the duration of the test in hours. Band A indicates the current (A), band B indicates the voltage (potential)) (V), band C depicts time differences (μs) in the ultrasonic pulse transmitted by the transducer (the "time of flight") and the receipt of the signal which had been transmitted through the test battery, and the band D depicts time differences (μs) in the ultrasonic pulse sent by the transducer (the "time of flight") and the receipt of the signal which had been reflected from the test battery. Band E includes two traces, each of the signal amplitude, the upper ('m") being the integrated (normalized) values at each time interval (0.008 hours) of the data of band D ("Reflected Signal"), and the lower ("n") being the integrated (normalized) value of each time interval (0.008 hours) of the data of band C ('transmitted signal"). Again, such data and information which is derived from the interrogation method and as is represented on bands C, D, and/or E represent useful pulse records, each of which may be correlated to known operating characteristics, e.g., voltage, amperage of the tested battery at any one or more points of time during the interrogation. Additionally data from one or more of bands C, D, and/or E and particularly traces n, m provide useful information and data which may be used by a processor means to also determine and/or predict the SOC and the SOH of the battery evaluated in the test, e.g. by comparison with a reference data set, or of a further test battery of the same battery type.

The invention claimed is:

1. A method of testing a battery, the method comprising:
   transmitting sound signals through at least a portion of a test battery from a first side of the test battery;
   creating a test data set for the test battery, the test data set comprising, for at least a first sound signal transmitted at a first time instance, at least one of:
      transmission time of flight values of the first sound signal measured at a second side of the test battery opposite to the first side, for a first duration of time after the first time instance; or
      reflection time of flight values of reflections of the first sound signal from the second side, measured at the first side, for a second duration of time after the first time instance;
   comparing at least one of the transmission time of flight values or the reflection time of flight values of the test data set with respective transmission time of flight values or reflection time of flight values of a reference data set; and
   determining, in a non-invasive manner, one or more characteristics of the test battery based on the comparison.

2. The method of claim 1, wherein the first sound signal is a single sound pulse or a set of two or more sound pulses.

3. The method of claim 1, wherein the one or more characteristics of the test battery comprise a state of charge (SOC) of the test battery.

4. The method of claim 3, wherein the SOC provides an indication of a charge condition of the test battery in a range between a fully discharged state and a fully charged state.

5. The method of claim 1, wherein the one or more characteristics of the test battery comprise a state of health (SOH) of the test battery.

6. The method of claim 5, wherein the SOH of the test battery provides an indication of a present condition of the test battery in relation to the reference data set.

7. The method of claim 5, further comprising predicting a future performance or lifetime of the test battery based on the SOH.

8. The method of claim 1, wherein the one or more characteristics of the test battery comprise changes in physical states of the test battery, wherein the physical states of the test battery comprise one or more of:
   density or elastic modulus of one or more internal components or parts of the test battery;

structural relaxation related transport phenomena based on one or more of open circuit potential, phase change, mechanical strain, internal fractures, swelling, or dissolution of one or more of the internal components of the test battery or deposition of materials upon one or more surfaces of one or more of the internal components of the test battery.

9. The method of claim 1, wherein comparing the test data set with the reference data set comprises one or more of:

a wavelet analysis of vectors between the test data set and the reference data set, comparing Fourier transforms between the test data set and the reference data set, or performing a Bayesian analysis of the test data set and the reference data set.

10. The method of claim 1, wherein the reference data set is representative of one or more physical states of a reference battery.

11. The method of claim 10, wherein the reference battery is the same as the test battery, with the test data set and the reference data set collected based on transmitting sound signals at different time instances, including the first time instance and one or more other time instances, through the test battery.

12. The method of claim 1, comprising creating the test data set during charge/discharge cycles of the test battery, such that the test data set is representative of the one or more characteristics of the test battery at different charge levels of the test battery.

13. The method of claim 1, comprising creating the test data set during a manufacturing process of the test battery, and based on the one or more characteristics, determining whether to: proceed with or complete the manufacturing process of the test battery; or to discard or reject the test battery from the manufacturing process.

14. The method of claim 1, comprising transmitting the sound signals from a sound source, receiving responses to the first sound signals at a one or more sound receivers at the second side and/or responses to the reflected sound signals at one or more sound receivers at the first side, and performing one or more of the steps of creating, comparing, and determining in a processor.

15. The method of claim 14, further comprising storing one or more of the reference data set, the test data set or a result of the comparison in a storage medium or the processor.

16. The method of claim 14, wherein one or more of the sound source or the sound receivers at the first side or the second side comprise ultrasonic transducers.

17. An apparatus comprising:

a test battery;

a transmitter configured to transmit sound signals including at least a first sound signal transmitted at a first time instance, through at least a portion of the test battery from a first side of the test battery;

at least one of, a first receiver on a second side of the test battery opposite to the first side and configured to receive responses to the first sound signal, or a second receiver on the first side of the test battery configured to receive responses to reflections of the first sound signal from the second side; and a processor configured to:

create a test data set for the test battery the test data set comprising:

transmission time of flight values of the first sound signal measured at the first receiver, for a first duration of time after the first time instance; or reflection time of flight values of the reflections of the first sound signal from the second side measured at the second receiver, for a second duration of time after the first time instance;

compare at least one of the transmission time of flight values or the reflection time of flight values of the test data set with respective transmission time of flight values or reflection time of flight values of a reference data set; and determine, in a non-invasive manner, one or more characteristics of the test battery based on the comparison.

18. The apparatus of claim 17, wherein one or more of the transmitter, the first receiver or the second receiver comprise sound transducers and wherein the first sound signal is a single sound pulse or a set of two or more sound pulses.

19. The apparatus of claim 17, wherein the one or more characteristics of the test battery comprise a state of charge (SOC) of the test battery, wherein the SOC provides an indication of a charge condition of the test battery in a range between a fully discharged state and a fully charged state.

20. The apparatus of claim 17, wherein the one or more characteristics of the test battery comprise a state of health (SOH) of the test battery, wherein the SOH of the test battery provides an indication of a present condition of the test battery in relation to the reference data set.

21. The apparatus of claim 20, wherein the processor is further configured to predict a future performance or lifetime of the test battery based on the SOH.

22. The apparatus of claim 17, wherein the one or more characteristics of the test battery comprise changes in physical states of the test battery, wherein the physical states of the test battery comprise one or more of:

density or elastic modulus of one or more internal components or parts of the test battery;

structural relaxation related transport phenomena based on one or more of open circuit potential, phase change, mechanical strain, internal fractures, swelling, or dissolution of one or more of the internal components of the test battery; or deposition of materials upon one or more surfaces of one or more of the internal components of the test battery.

23. The apparatus of claim 17, wherein the processor is configured to compare the test data set with the reference data set based on:

a wavelet analysis of vectors between the test data set and the reference data set, a comparison Fourier transforms between the test data set and the reference data set, or a Bayesian analysis of the test data set and the reference data set.

24. The apparatus of claim 17, wherein the reference data set is representative of one or more physical states of a reference battery.

25. The apparatus of claim 17, wherein the test data set is representative of the one or more characteristics of the test battery at different charge levels of the test battery.

26. The apparatus of claim 17, wherein the processor is configured to create the test data during a manufacturing process of the test battery, and wherein the processor is further configured to: determine, based on the one or more characteristics, whether to proceed with or complete the manufacturing process of the test battery; or to discard or reject the test battery from the manufacturing process.

27. An apparatus comprising:

a test battery;

means for transmitting sound signals including at least a first sound signal transmitted at a first time instance, through at least a portion of the test battery from a first side of the test battery;
at least one of a first means for receiving responses to the first sound signal at a second side opposite to the first side, or a second means for receiving responses to reflections of the first sound signal from the second side, at the first side;
means for creating a test data set for the test battery, the test data set comprising:
  transmission time of flight values of the first sound signal measured at the first means for receiving, for a first duration of time after the first time instance; or
  reflection time of flight values of the reflections of the first sound signal from the second side measured at the second receiver, for a second duration of time after the first time instance;
means for comparing at least one of the transmission time of flight values or the reflection time of flight values of the test data set with respective transmission time of flight values or reflection time of flight values of a reference data set; and
means for determining, in a non-invasive manner, one or more characteristics of the test battery based on the comparison.

28. A non-transitory computer-readable storage medium comprising instructions, which, when executed by a processor, causes the processor to perform operations for testing a battery, the non-transitory computer-readable storage medium comprising:
  instructions for transmitting sound signals through at least a portion of a test battery from a first side of the test battery;
  instructions for creating a test data set for the test battery, the test data set comprising, for at least a first sound signal transmitted at a first time instance, at least one of:
    transmission time of flight values of the first sound signal measured at a second side of the test battery opposite to the first side, for a first duration of time after the first time instance; or
    reflection time of flight values of reflections of the first sound signal from the second side, measured at the first side, for a second duration of time after the first time instance;
  instructions for comparing at least one of the transmission time of flight values or the reflection time of flight values of the test data set with respective transmission time of flight values or reflection time of flight values of a reference data set; and
  instructions for determining, in a non-invasive manner, one or more characteristics of the test battery based on the comparison.

29. A method of testing a battery, the method comprising:
transmitting sound signals through at least a portion of a test battery and receiving response signals responsive to the transmitted sound signals;
creating a test data set for the test battery comprising two or more test data points, the two or more test data points being representative of physical states of the test battery, the physical states correlated to the response signals;
comparing the test data set with a reference data set comprising two or more reference data points; and
determining, in a non-invasive manner, one or more characteristics of the test battery based on the comparison, wherein the one or more characteristics of the test battery comprise a state of charge (SOC) of the test battery.

30. A method of testing a battery, the method comprising:
transmitting sound signals through at least a portion of a test battery and receiving response signals responsive to the transmitted sound signals;
creating a test data set for the test battery during charge/discharge cycles of the test battery, the test data set comprising two or more test data points, the two or more test data points being representative of physical states of the test battery at different charge levels of the test battery, the physical states correlated to the response signals;
comparing the test data set with a reference data set comprising two or more reference data points; and
determining, in a non-invasive manner, one or more characteristics of the test battery based on the comparison.

* * * * *